United States Patent
Sankhala et al.

(10) Patent No.: US 12,310,725 B2
(45) Date of Patent: May 27, 2025

(54) HIGH DENSITY ANALOG MULTIPEXING

(71) Applicant: EnLiSense, LLC, Allen, TX (US)

(72) Inventors: Devangsingh Gajendarsingh Sankhala, Richardson, TX (US); Sriram Muthukumar, Allen, TX (US)

(73) Assignee: EnLiSense LLC, Allen, TX (US)

( * ) Notice: Subject to any disclaimer, the term of this patent is extended or adjusted under 35 U.S.C. 154(b) by 1230 days.

(21) Appl. No.: 16/543,499

(22) Filed: Aug. 16, 2019

(65) Prior Publication Data

US 2020/0054259 A1  Feb. 20, 2020

Related U.S. Application Data

(60) Provisional application No. 62/719,387, filed on Aug. 17, 2018.

(51) Int. Cl.
*H03M 1/66* (2006.01)
*A61B 5/00* (2006.01)
*A61B 5/145* (2006.01)
*H03H 7/00* (2006.01)

(52) U.S. Cl.
CPC ........ *A61B 5/14546* (2013.01); *A61B 5/0002* (2013.01); *A61B 5/6801* (2013.01); *H03H 7/00* (2013.01); *H03M 1/66* (2013.01); *A61B 2562/06* (2013.01)

(58) Field of Classification Search
CPC . A61B 5/14546; A61B 5/0002; A61B 5/6801; A61B 2562/06; H03H 7/00; H03M 1/66
See application file for complete search history.

(56) References Cited

U.S. PATENT DOCUMENTS

| | | | |
|---|---|---|---|
| 10,006,882 B2 | 6/2018 | Prasad et al. | |
| 2003/0089899 A1* | 5/2003 | Lieber | H01L 29/0665 257/E29.081 |
| 2014/0147336 A1* | 5/2014 | Ching | G01N 33/5438 422/69 |
| 2014/0235463 A1* | 8/2014 | Rothberg | G01N 27/4148 506/38 |
| 2016/0091511 A1* | 3/2016 | Di Tullio | B01L 3/502715 435/13 |
| 2016/0238553 A1* | 8/2016 | Shachar | G01N 27/4145 |
| 2017/0288655 A1* | 10/2017 | He | H03K 5/131 |
| 2017/0315076 A1* | 11/2017 | Morgan | A61B 5/7221 |
| 2018/0333587 A1* | 11/2018 | Howard | A61B 5/0006 |

(Continued)

OTHER PUBLICATIONS

Kim, Jaemin, A wearable multiplex silicon nonvolatile memory array using nanocrystal charge confinement. Science Advances. Jan. 2016; vol. 2, Issue 1. doi: 10.1126/sciadv.1501101, https://www.science.org/doi/full/10.1126/sciadv.1501101. (Year: 2016).*

*Primary Examiner* — Alex M Valvis
*Assistant Examiner* — Grace L Rozanski
(74) *Attorney, Agent, or Firm* — Aambell PC

(57) ABSTRACT

Systems, methods, and devices include a high-density analog multiplexer topology. Such topologies can be used, for example, in sensor device applications. An analog multiplexer circuit can include circuitry to receive N input signals; and circuitry to generate N selection signals for selecting one of said N data signals to be output from said analog multiplexer circuit. The analog multiplexer comprises one or more analog impedances.

20 Claims, 19 Drawing Sheets

(56) References Cited

U.S. PATENT DOCUMENTS

2018/0338696 A1\* 11/2018 Deliwala .............. A61B 5/6801
2019/0250153 A1\* 8/2019 Muthukumar ..... G01N 33/5438
2020/0405204 A1\* 12/2020 Howard ............. A61B 5/14546
2021/0164910 A1\* 6/2021 Jones ................. G01N 33/5302

\* cited by examiner

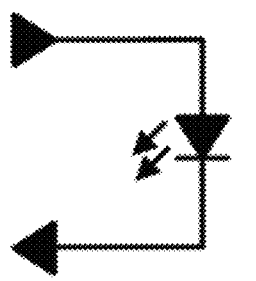
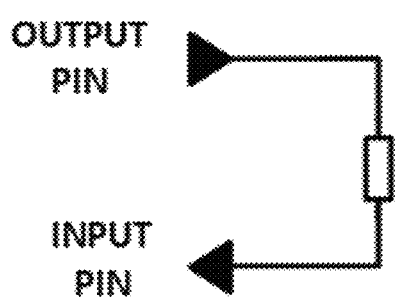
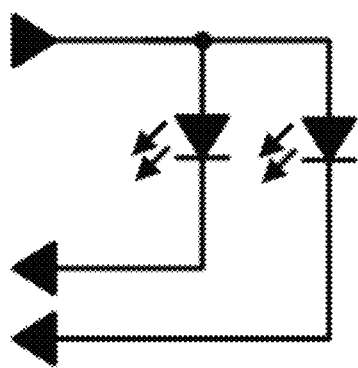
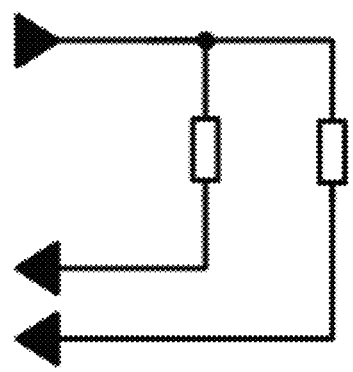
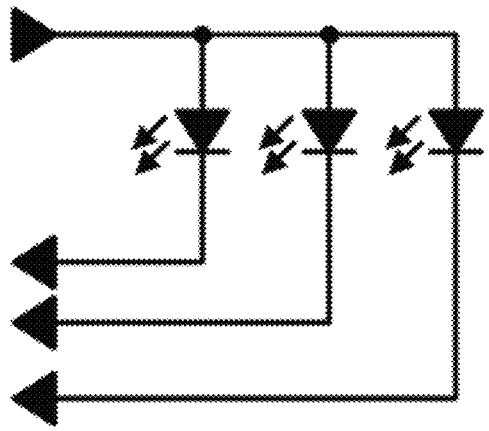
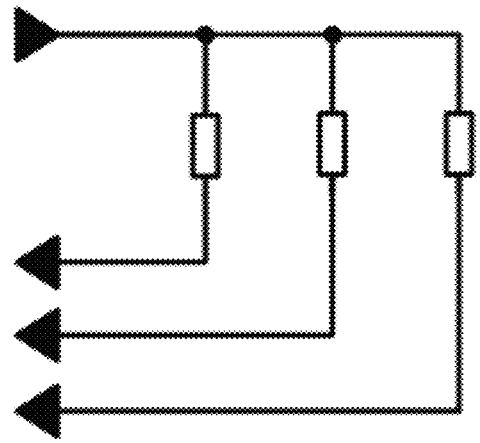
*FIG. 2A*          *FIG. 2B*
1:N MULTIPLEXING DIGITAL LOAD     ANALOG LOAD
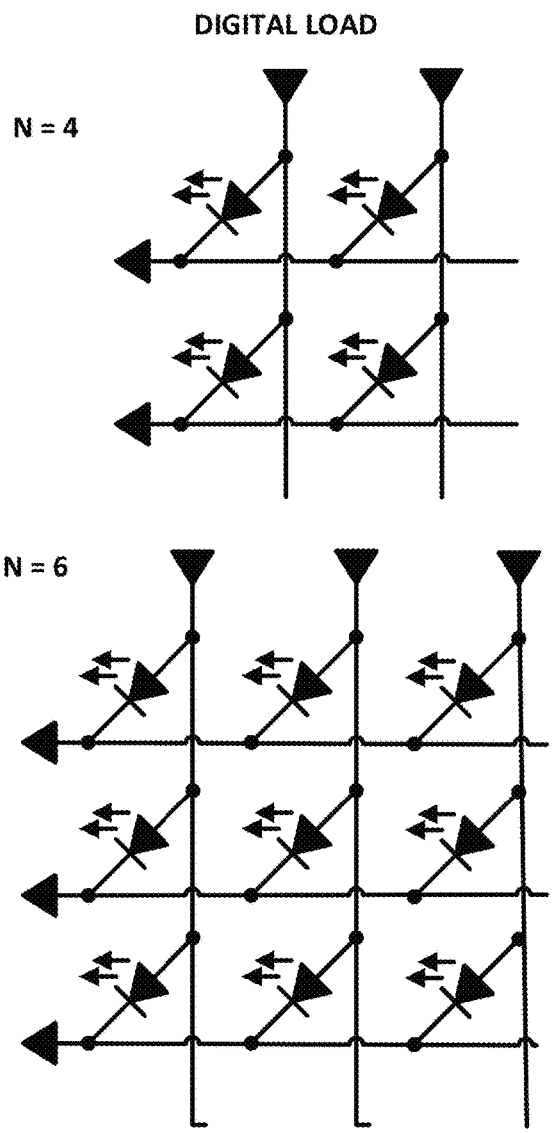
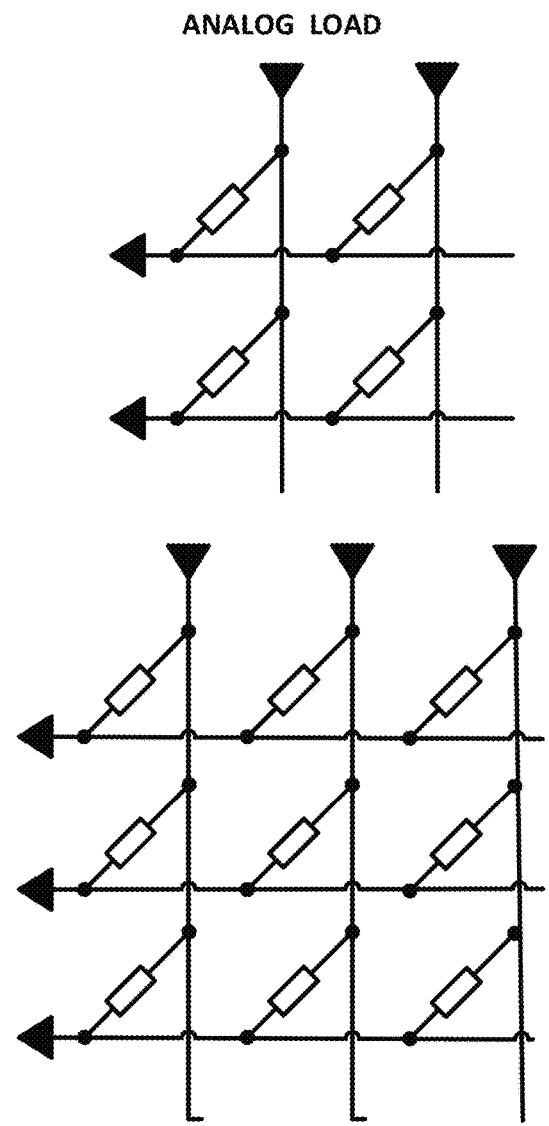
*FIG. 3A*  *FIG. 3B*
N/2:N/2 MULTIPLEXING/ ROW-COLUMN DECODER

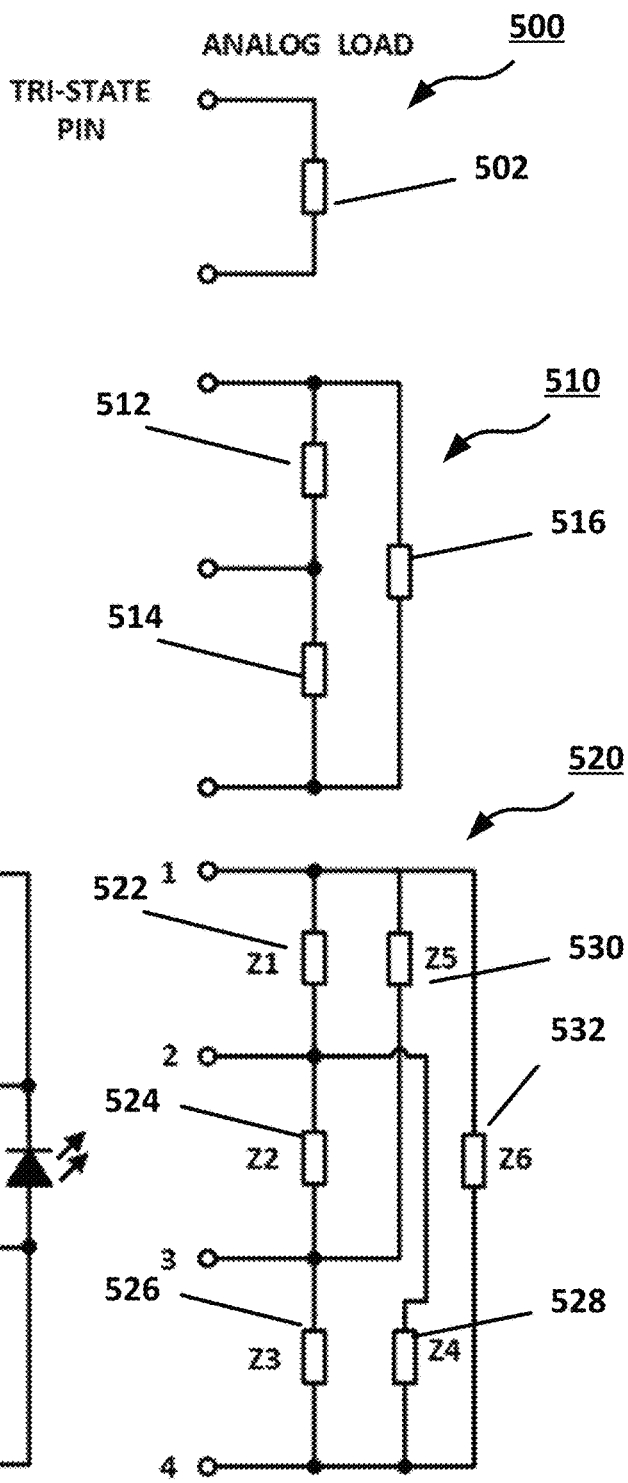
FIG. 5A "CHARLIEPLEXING" SCHEME
FIG. 5B HDAM SCHEME

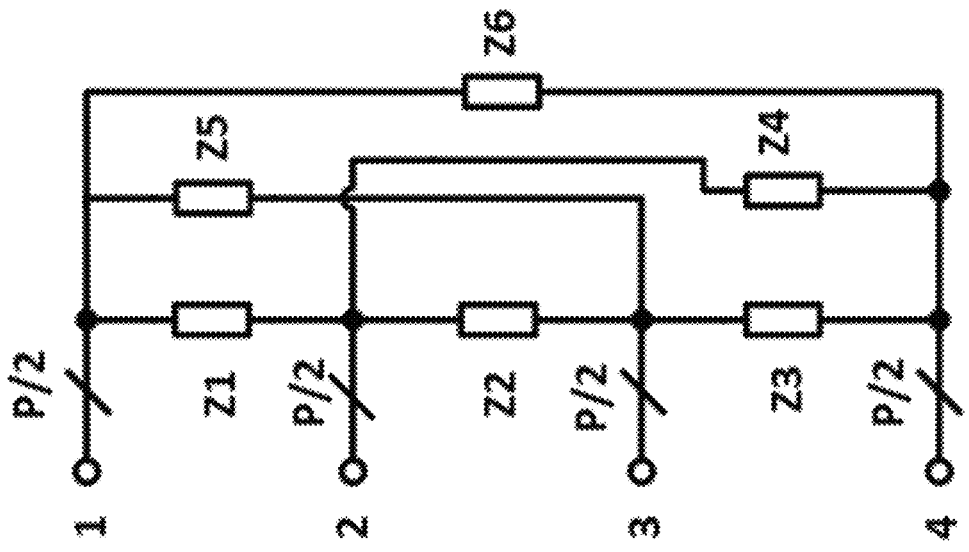
*FIG. 5D*  P-WIRE HDAM SCHEME
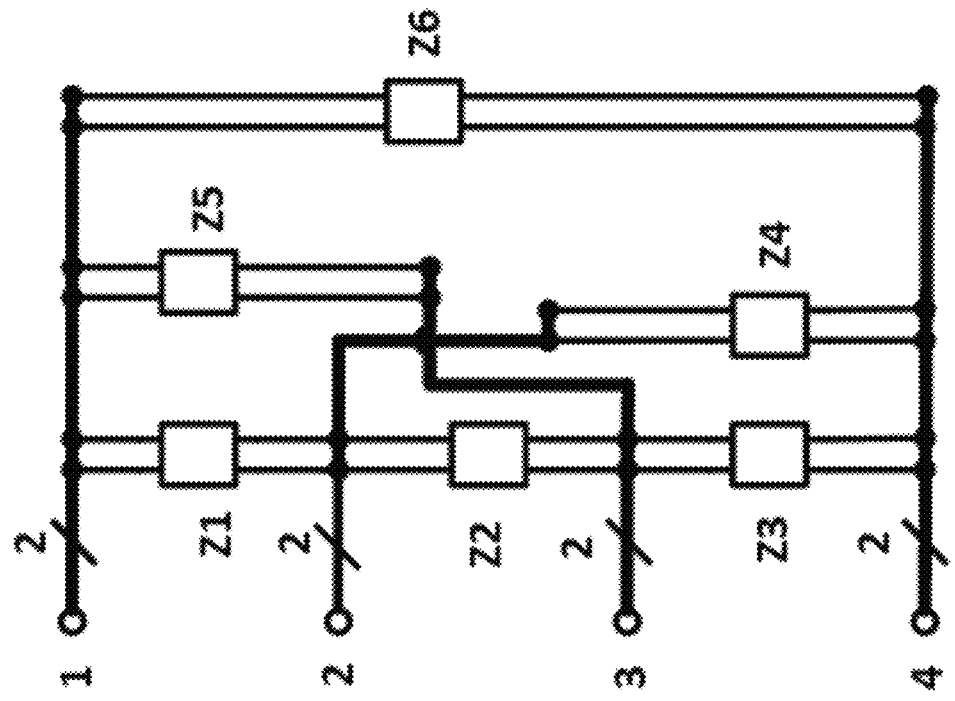
*FIG. 5C*  4-WIRE HDAM SCHEME

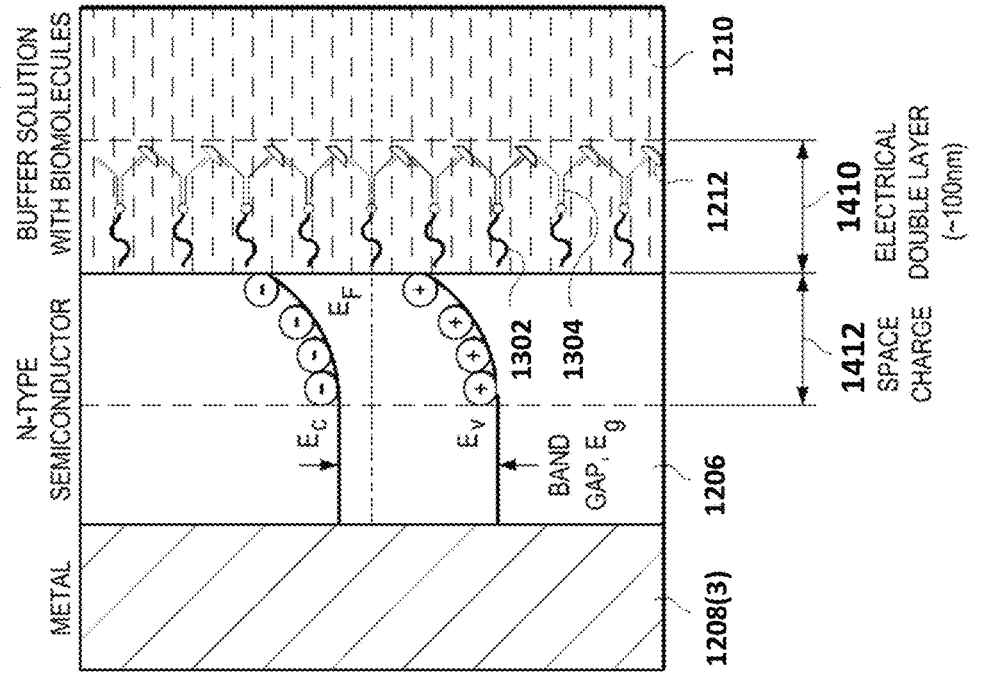
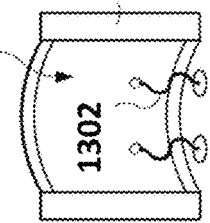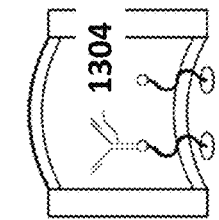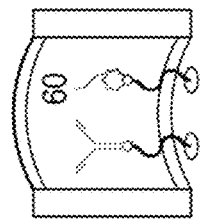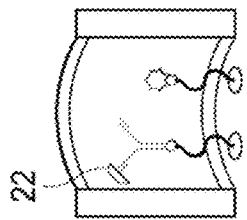
FIG. 14

HIGH DENSITY ANALOG MULTIPEXING

CROSS REFERENCE TO RELATED APPLICATION

Pursuant to 35 U.S.C. § 119(e), this application claims the benefit of U.S. Provisional Patent Ser. No. 62/719,387 filed on Aug. 17, 2019, the contents of which are incorporated by reference herein in its entirety.

BACKGROUND

Wearable devices can incorporate various analog and digital sensors for measuring motion, heart rate, activity levels, sleep, etc. The use of sensors can result in the collection of enormous amounts of biological, medical, and other data.

Multiplexed digital sensor schemes use digital multiplexers because digital multiplexers are robust in view of noise due to the dual-logic state operation (i.e., 0 and 1 logic signal states, where high impedance (HiZ) not being a signal state). This helps with the ease of implementation of large-scale, wired digital sensor networks independent of the signaling protocol, as they are immune to noise levels comparable to the supply voltage.

BRIEF DESCRIPTION OF THE DRAWINGS

FIGS. 2A-B are schematic diagrams illustrating digital and analog multiplexing schemes, respectively.

FIGS. 3A-B are schematic diagrams of digital and analog N/2:N/2 multiplexing decoder designs, respectively.

FIG. 5A is a schematic diagram of an example digital charlieplexing topology.

FIGS. 5B-D are schematic diagrams of example high-density analog multiplexing topologies in accordance with embodiments of the present disclosure.

FIG. 14 is a schematic diagram illustrating example operations and details according to an embodiment of a biosensing system as shown in FIGS. 12A-C.

Figures are not drawn to scale.

DETAILED DESCRIPTION

Implementation of a large-scale analog sensor network, in contrast to digital sensor networks, are challenging as analog signals may not be as large as the supply voltage and are prone to higher noise levels. Analog multiplexers are used to alleviate the large throughput problem, although they are designed relatively larger in size to allow mitigation of harmonic distortion, noise, charge injection, and resistive signal drop. Moreover, use of analog multiplexers can lead to large capacitive loads for the driver and loop instability. Such issues can result in higher power consumption, which is not suitable for low-power systems such as portable or wearable systems that use battery-based power sources, etc. This disclosure describes multiplexed systems using analog sensor networks for wearable device systems using fewer source and sink pins to conserve board and/or silicon, component spaces while also reducing the burden on system power consumption.

Figure 1:
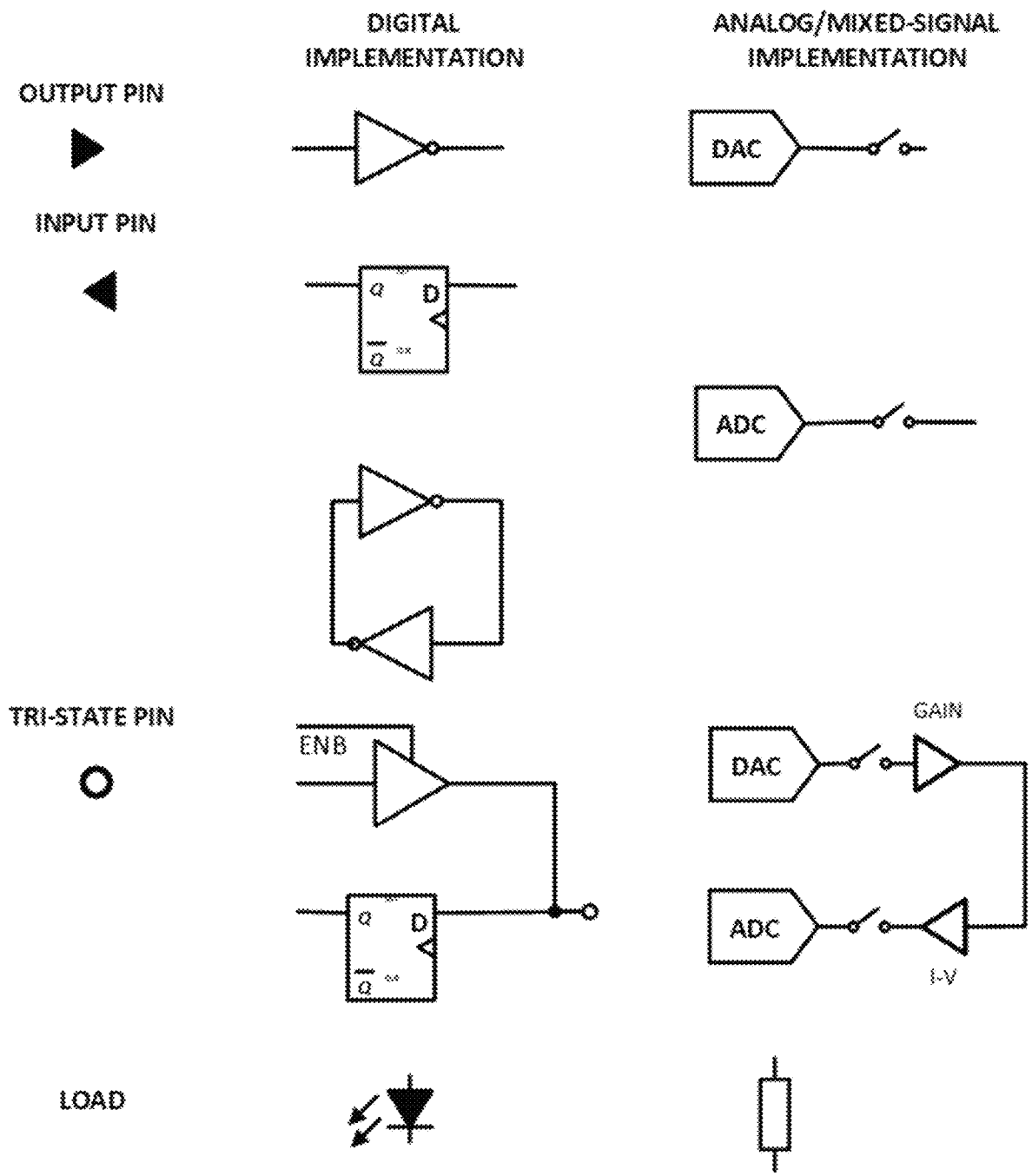
FIG. 1 is a schematic diagram illustrating example electronic components in accordance with embodiments of the present disclosure.

A typical load connected to a source uses two wires, one connection as a source and one as a sink or return. For sensing or display mechanisms, certain commonly known circuit entities will be used to discuss multiplexing schemes as shown in FIG. 1. FIG. 1 is a schematic diagram illustrating various pins in a electrical circuit. An output pin is an element that drives a load, whereas an input pin is an element in the circuit that is driven by the load. In any generic circuit architecture (or diagram), the output pin is followed by the load, which is followed by the input pin (discounting intervening elements).

A digital output pin is backed by an inverter or a buffer, whereas an analog output pin can be backed by an AC generator, digital to analog converter (DAC), phase locked loop (PLL), or any other similar source. A digital input pin may drive a D flip flop or an SRAM cell, whereas an analog input pin may drive an S/H circuit, I-V amplifier or direct couple to an analog to digital converter (ADC).

For simplicity, a digital load is assumed to be a light emitting diode (LED), whereas it is assumed that an alternating current (AC) load may be any combination of impedance elements. In the present disclosure, impedance can include resistance (R), inductance (L), capacitance (C), or a combination of R, L, and/or C. Since an objective of the present disclosure is to highlight higher load count sensing, the terms multiplexing and demultiplexing may be used interchangeably.

FIG. 2A is a schematic diagram illustrating an example implementation of 1:N multiplexing for a digital load driven by mathematical induction. FIG. 2B is a schematic diagram illustrating an example implementation of 1:N multiplexing for analog load drive by mathematical induction. In a 1:N (or N:1) multiplexed (demultiplexed) system, a typical schematic representation for multiple load connections can be as shown in FIG. 2A, where either source or sink terminals can be multiplexed, keeping the other terminal common. A similar analog multiplexed sensing scheme can be implemented with relative ease in electrical design and manufacturing complexity as shown in FIG. 2B. For M loads, the hardware wiring complexity is M+1 rather than 2M in case of a regular M load parallel sensing scheme. This accounts for a 50% reduction in wiring in comparison to the parallel load sensing scheme.

The throughput of a multiplexing architecture is significantly increased using a digital row-column decoder scheme (N/2:N/2 or N1:N2) where larger number of input and output pins are used. Here, it is assumed that the total number of available pins, irrespective of input or output function, is the same to compare density performance with other multiplexing schemes discussed. FIG. 3A is a schematic diagram of an example implementation of N/2:N/2 multiplexing for digital load drive by mathematical induction. FIG. 3B is a schematic diagram of an example implementation of N/2:N/2 multiplexing for analog load drive by mathematical induction. As shown in FIGS. 3A and 3B, if the output pins are the columns and the input pins are rows, a selection of the load can be done based on the row and column number to sense a load at a specific location in the load matrix. The wiring complexity of this system will be 2N2 or 2(N1+N2)) based on the total number of pins used for creating the load matrix, independent of the number of loads.

Figure 4A:
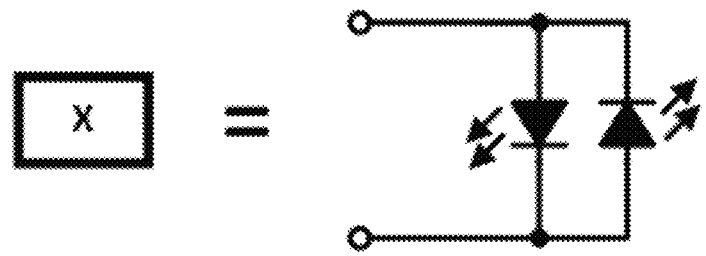
FIGS. 4A-B are schematic diagrams of anti-parallel digital loads.
Figure 4B:
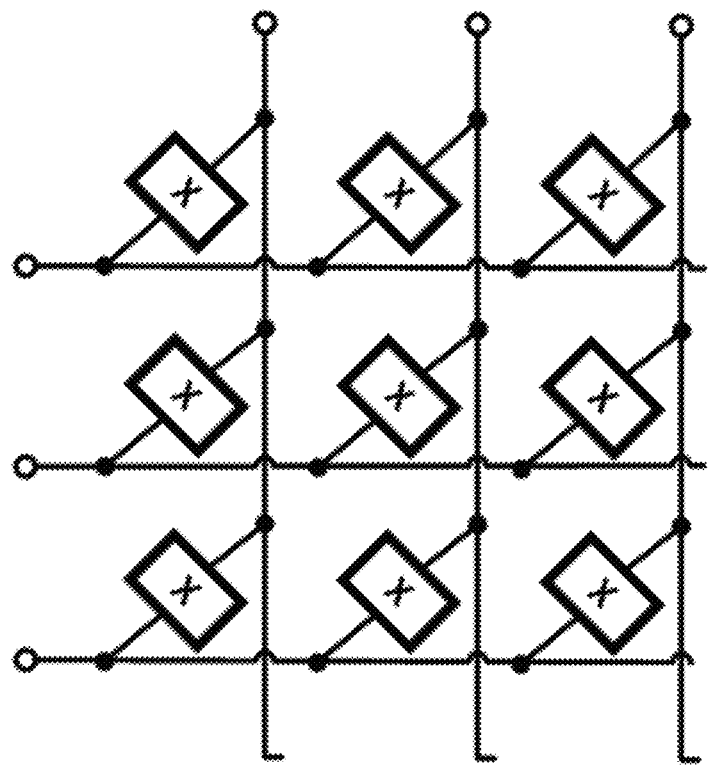

FIG. 4A is an example of anti-parallel loading using LEDs. FIG. 4B is a schematic diagram of an example implementation of N/2:N/2 multiplexing for digital load drive for anti-parallel loading. In case of digital loads, since complementary drive is possible between 2 loads due to unidirectional current flow, thus an extension of this scheme is shown in FIG. 4B where anti-parallel LED connection is used. An advantage ratio is the qualitative improvement offered by a new technique over and old technique of multiplexing. This scheme cannot be applied directly to an analog sensor network or an AC loads for two reasons: (a) Two parallel impedance elements will result in a combined impedance element; (b) If one analog load is driven, a considerable part of the excitation will pass to the other loads due to the resulting residual series-parallel combination formed by the other impedance elements. This will lead to inaccuracies in measurement.

FIG. 5A is a schematic diagram of example digital charlieplexing topologies. Charlieplexing is a technique for driving a multiplexed display in which relatively few I/O pins on a microcontroller are used e.g., to drive an array of LEDs. Charlieplexing uses the tri-state logic capabilities of microcontrollers in order to gain efficiency over traditional multiplexing. Three-state, tri-state, or 3-state logic allows an output port to assume a high impedance state, effectively removing the output from the circuit, in addition to the 0 and 1 logic levels. This allows multiple circuits to share the same output line or lines (such as a bus which cannot listen to more than one device at a time). Although Charlieplexing technologies are more efficient in their use of I/O, there are issues that cause Charlieplexing technologies to be more complicated to design and render it impractical for larger displays. These issues include duty cycle, current requirements, and the forward voltages of the LEDs.

When using Charlieplexing, n drive pins can drive N digits with N−1 segments. When simplified, Charlieplexing topologies equate to N pins being able to drive $N^2-N$ segments or LEDs. Traditional multiplexing takes many more pins to drive the same number of LEDs; 2N pins must be used to drive $N^2$ LEDs (though a 1-of-N decoder chip can be used to reduce the number of microcontroller I/O pins to N+log 2(N)).

This disclosure describes, in part, High-density Analog Multiplexing (HDAM) and where the analog multiplexing scheme does not use antiparallel loads. FIG. 5B is a schematic diagram of example HDAM topologies 500, 510, and 520 in accordance with embodiments of the present disclosure. FIG. 5B illustrates several possible combinations for connecting the maximum number of loads.

Starting with example topology 500, a single load/impedance 502 can be coupled to a tri-state pin. The tri-state pin I/O in this example topology can include a DAC coupled to a switch prior to a gain element, such as an amplifier circuit element, as shown by example in FIG. 1. Topology 510 can include a tri-state pin I/O, with N=3 pins that can support three loads 512, 514, 516, as shown. Topology 520 can include a tri-state pin I/O, with N=4 that can support 6 loads, 522, 524, 526, 528, 530, and 532, as shown in FIG. 5B. The loads can be sensor loads. The plurality of sensor loads can be coupled to the high-density analog multiplexer network. The plurality of sensors can be configured to detect a plurality of analytes. The plurality of sensors can include, for example, a first set of one or more sensor loads to detect a first analyte. The plurality of sensors can include a second set of one or more sensors to detect a second analyte, the first analyte being different from the second analyte. More analytes than two can be detected by the sensor loads.

Thus, the number of loads that can be connected to the proposed N pin multiplexer is (N(N−1))/2. By contrast, N loads can be connected to a standard 1:N multiplexing system. To connect M analog loads, the system can use $\{1+\sqrt{(1+4M)}\}/4$ pins. Thus, the wiring complexity or space polynomial of this HDAM multiplexing scheme or the number of loads to be connected increases as $M(N^2-N)$. This scheme can also be extrapolated to loads that are driven and/or sensed using 4-wire or P-wire configurations as shown in FIGS. 5C and 5D, respectively. The various analog loads shown in FIG. 5B-5D can replace the digital load shown in FIG. 4A. FIG. 4B can be implemented using the various analog load configurations shown in FIGS. 5B, 5C, and 5D. The load topologies for the 3, 4, . . . P wire configurations can be defined in a similar way as that shown in FIG. 5B.

Table 1 provides a comparative analysis of the HDAM scheme (our innovation) with the various currently used multiplexing schemes.

TABLE 1

A comparison of various multiplexing schemes.

| Features | 1:N<br>N = total number of source/sink pins | N1:N2 → N/2:N/2<br>N1 = number of row source/sink pins<br>N2 = number of column sink/source pins<br>N = total number of source/sink pins | nCPLEX<br>N = number of bidirectional digital pins | HDAM<br>N = number of bidirectional digital or analog pins |
|---|---|---|---|---|
| M = Number of loads driven/sensed | M = N − 1 | M = N1 × N2 → $N^2/4$ | M = $N^2$ − N | $M = \dfrac{N^2 - N}{2}$ |
| Total number of pins (or circuit nodes) | N | (N1 + N2) → N | N | N |
| Number of loads per pin (or node) | $\dfrac{N-1}{N}$ | $\dfrac{N1 \times N2}{N1 + N2} \to \dfrac{N}{4}$ | N − 1 | $\dfrac{(N-1)}{2}$ |
| Type for Loads | Analog and Digital | Analog and Digital | Digital Only | Analog and Digital |
| Undesirable excitation for Analog Loads | Does not exist due to other loads being parallel and HiZ | Does not exist due to other loads being parallel and HiZ | Not Applicable | Exists due to other loads in series-parallel combination |
| Corrective action for undesirable excitation | Not required | Not required | Not Applicable | System of linear equation |

Table 2 provides the truth table for impedance-based sensing using the HDAM scheme for 4 bidirectional pins.

| Pin 1 | Pin 2 | Pin 3 | Pin 4 | Impedance to be driven/sensed |
|---|---|---|---|---|
| Source/Sink | Sink/Source | HiZ | HiZ | Z1 |
| HiZ | Source/Sink | Sink/Source | HiZ | Z2 |
| HiZ | HiZ | Source/Sink | Sink/Source | Z3 |
| HiZ | Source/Sink | HiZ | Sink/Source | Z4 |
| Source/Sink | HiZ | Sink/Source | HiZ | Z5 |
| Source/Sink | HiZ | HiZ | Sink/Source | Z6 |

High impedance can be defined as a point in a circuit (a node) that allows a relatively small amount of current through compared to other impedances, per unit of applied voltage at that point. High impedance circuits are low current and potentially high voltage, whereas low impedance circuits are the opposite (low voltage and potentially high current). Numerical definitions of "high impedance" vary by implementation or usage.

In analog circuits, a high impedance node can be one that does not have low impedance paths to any other nodes (e.g., in the frequency range being used by the circuit). High impedance nodes may have higher thermal noise voltages and are more prone to capacitive and inductive noise pick up. The HiZ elements, therefore, can be selectively used when considering other impedances or loads for sensor applications. When testing, they are often difficult to probe as the impedance of an oscilloscope or multimeter can heavily affect the signal or voltage on the node. High impedance signal outputs are characteristic of some transducers (such as crystal pickups); they require a very high impedance element from the amplifier to which they are connected. Vacuum tube amplifiers, and field effect transistors more easily supply high-impedance inputs than bipolar junction transistor-based amplifiers, although current buffer circuits or step-down transformers can match a high-impedance input source to a low impedance amplifier.

High impedance inputs are preferred on measuring instruments such as voltmeters or oscilloscopes. In audio systems, a high-impedance input may be required for use with devices such as crystal microphones or other devices with high internal impedance.

Figure 6A:
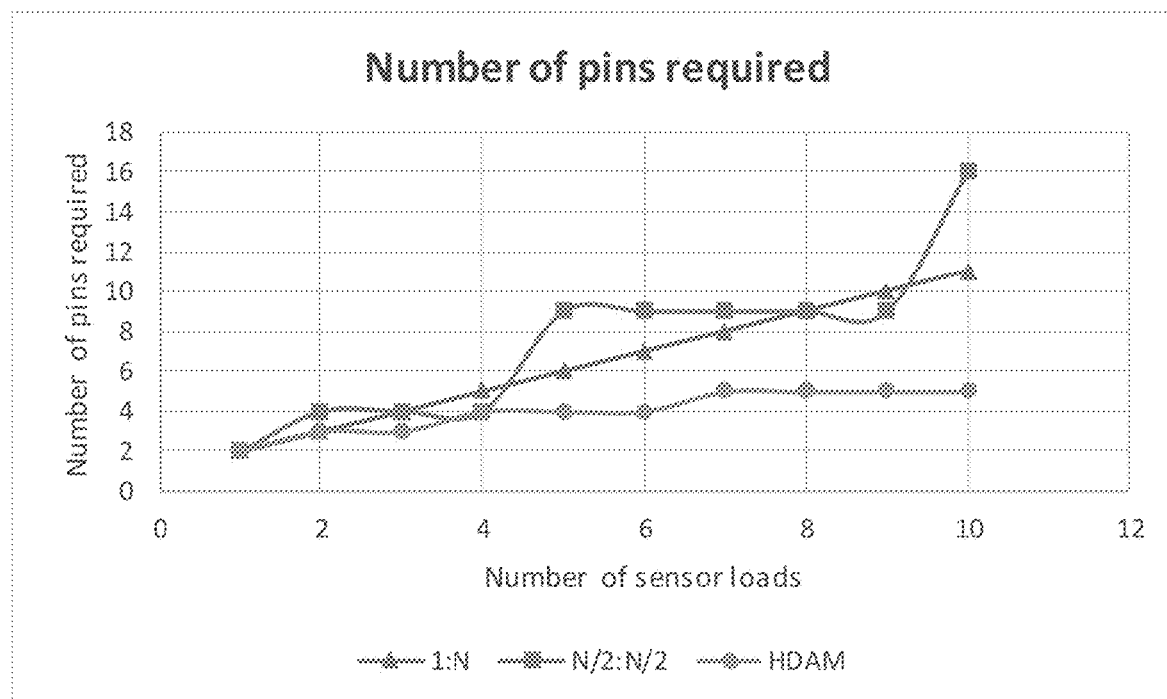
FIGS. 6A-6B are graphs indicating the advantages of embodiments of the present disclosure.
Figure 6B:
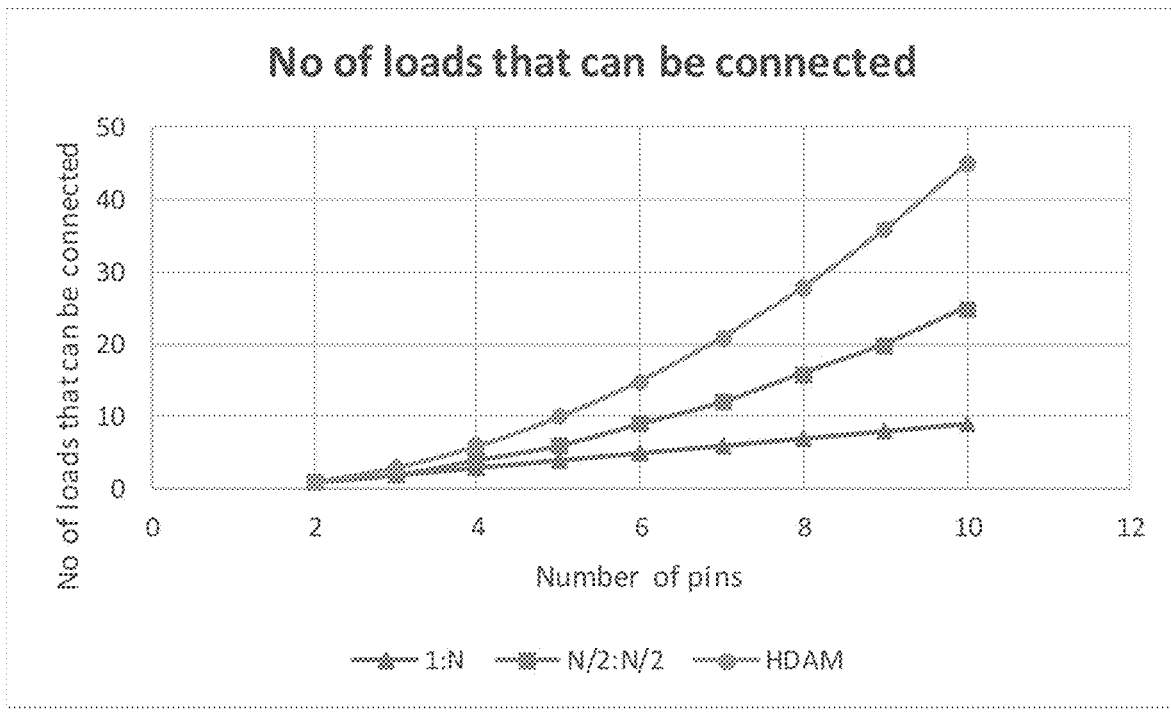
Figure 7A:
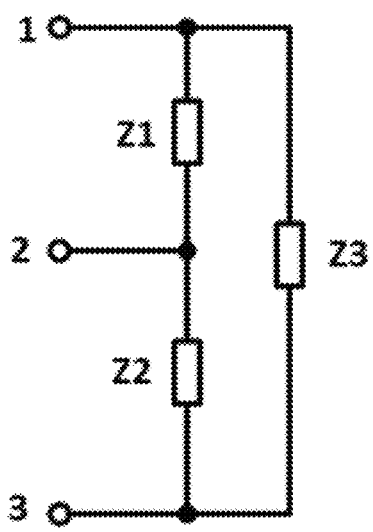
FIGS. 7A-D are schematic diagrams illustrating logical circuit diagrams of various input/output implementations of a 3 pin high-density analog multiplexer in accordance with embodiments of the present disclosure.
Figure 7B:
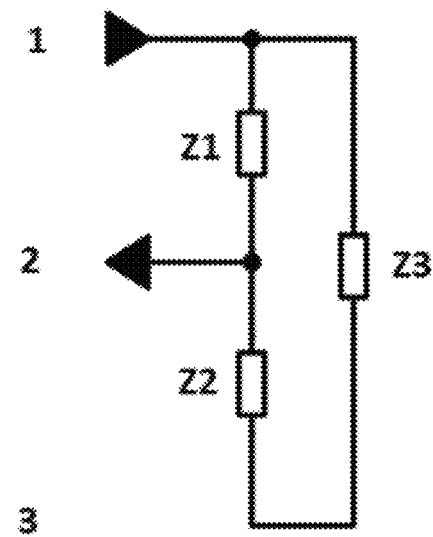
Figure 7C:
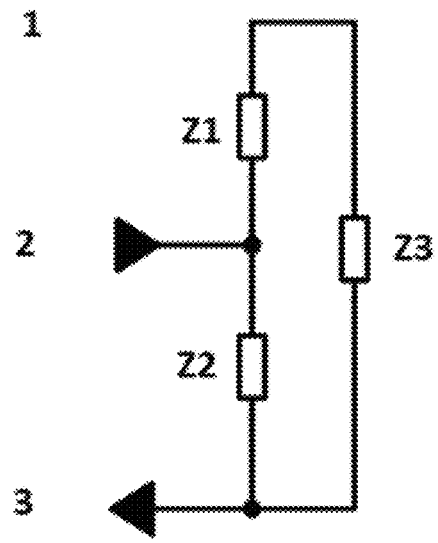
Figure 7D:
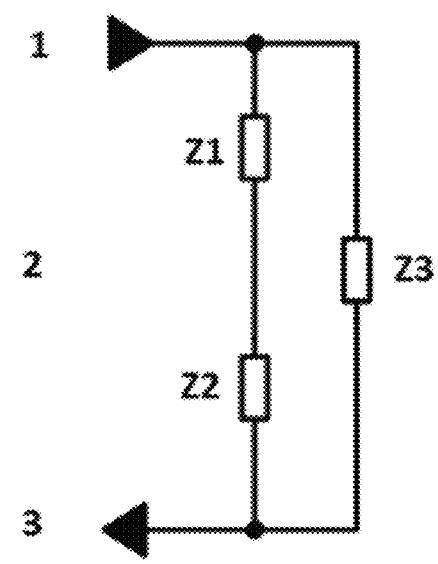

A comparison of the above-mentioned multiplexing schemes and the benefits offered by HDAM scheme in multiplexing higher sensor loads using fewer pins is evident from the calculated results shown in FIGS. 6A-B. The growth of the number of pins is minimal for an HDAM scheme, whereas the number of serviced impedance elements grows faster. This benefit results in multiple parallel combination of sensor loads that comes in parallel with the load impedance to be measured in the HDAM scheme. This parallel combination increases with the same rate as the number of sensor loads and could cause a huge error in measurement if not eliminated.

FIGS. 7A-D show such a manifestation of error from a 3-pin HDAM system. This inherent error can be eliminated by using a system of linear equations (1) to (6) below. First, the load Z1 is measured and the measured value is noted as C1, which is equivalent to Z1∥(Z2+Z3). The same is done for Z2 and Z3 to obtain C2 and C3. Since the wiring topology is known, the impedance seen by the control loop is as below:

$$C1 = Z1 \| (Z2 + Z3) \tag{1}$$

$$C2 = Z2 \| (Z1 + Z3) \tag{2}$$

$$C3 = Z3 \| (Z1 + Z2) \tag{3}$$

Solving the above equations for Z1, Z2 and Z3. Similar analysis would need to be done for n≥3 pin HDAM system.

$$Z1 = \frac{C1^2 + 2 \cdot C1 \cdot C2 + 2 \cdot C1 \cdot C3 - C2^2 + 2 \cdot C2 \cdot C3 - C3^2}{2(-C1 + C2 + C3)} \quad (4)$$

$$Z2 = \frac{C1^2 + 2 \cdot C1 \cdot C2 + 2 \cdot C1 \cdot C3 - C2^2 + 2 \cdot C2 \cdot C3 - C3^2}{2(C1 - C2 + C3)} \quad (5)$$

$$Z3 = \frac{C1^2 + 2 \cdot C1 \cdot C2 + 2 \cdot C1 \cdot C3 - C2^2 + 2 \cdot C2 \cdot C3 - C3^2}{2(C1 + C2 - C3)} \quad (6)$$

A high-density analog multiplexing scheme/topology/architecture implemented for single, differential or multi-wire excitation/sensing load systems which may be referred to as HDAM (High-density Analog Multiplexing) that allows for multiplexing higher number of sensor loads using fewer pins relative to other architecture schemes as shown in FIGS. 6A and 6B.

HDAM schemes described above can be implemented using discrete multichannel analog to digital converter (ADC) and/or a digital to analog converter (DAC) with the (tri-state) pinouts as shown in the FIGS. 5B, 5C, and 5D and can be applied directly to any analog sensor network or AC (alternating current) loads without causing errors or inaccuracies in measurements.

Commercial application of HDAM systems in any analog, power, RF, or mixed-signal application using microcontrollers, FPGAs, PLCs or equivalent; including but not limited to wearable, tabletop, rack-mount sensor and test and measurement systems for applications including but not limited to electrochemical sensors, biochemical sensors irrespective of sensing methodology and generic impedance measurements.

Use of a digital Fourier transform for rapid impedance extraction for various HDAM schemes.

Estimation of true impedance connected to a channel by nullifying the contribution of undesired parallel combination effects using a system of linear equations for various HDAM schemes.

Aspects of the embodiments are not limited to analog-only multiplexers. The configurations shown herein can be extended to digital and/or digital+analog multiplexers. For example, digital and/or analog sensor loads can be used in parallel or anti-parallel in multiplexing decoder circuitry.

Figure 8A:
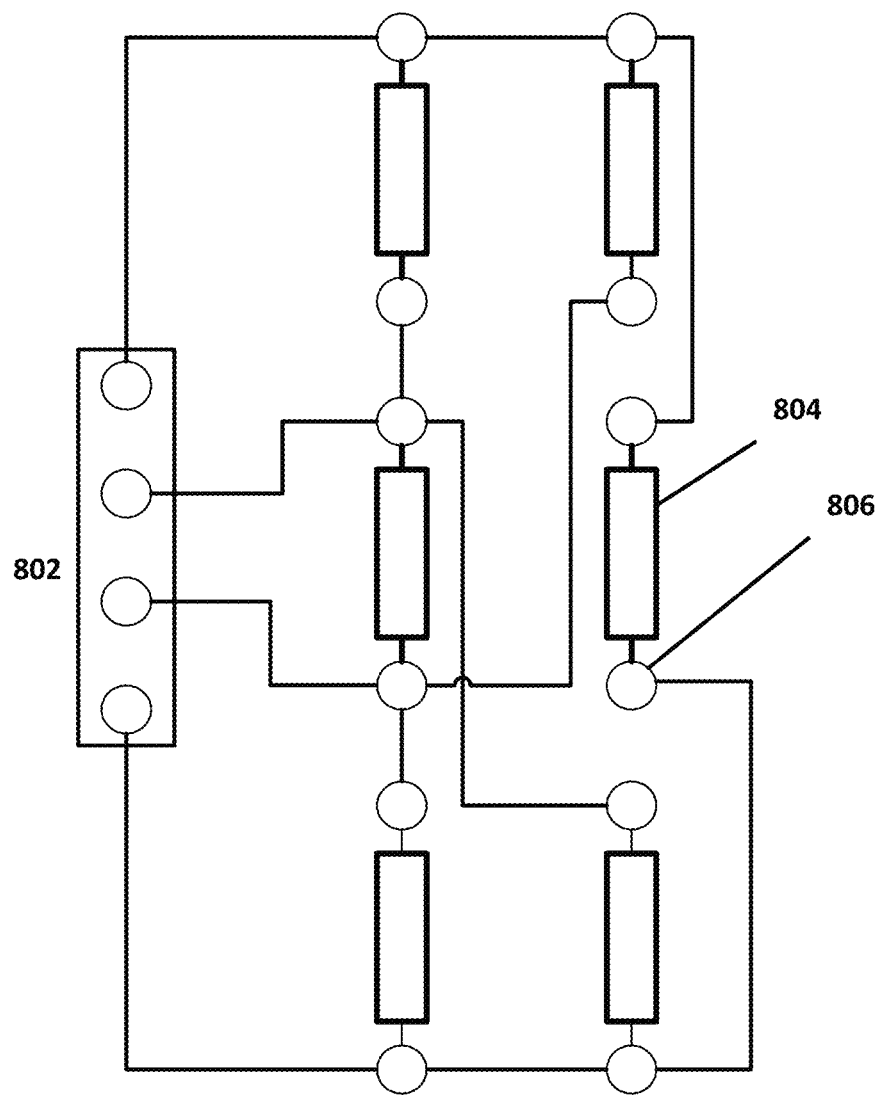
FIG. 8A is a schematic diagram of an example high-density analog multiplexer routing for N=4 pins in accordance with embodiments of the present disclosure.
Figure 8B:
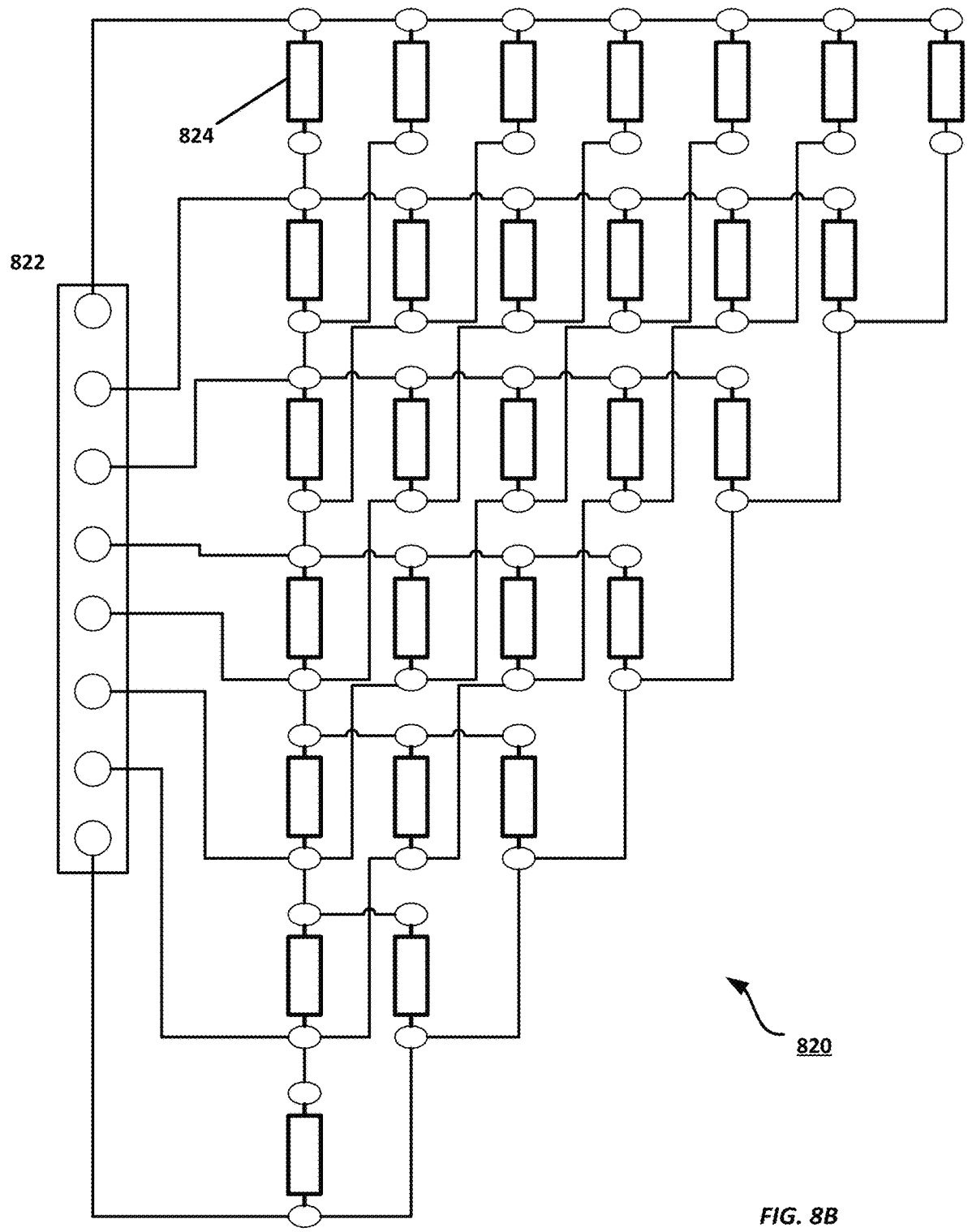
FIG. 8B is a schematic diagram of an example high-density analog multiplexer routing for N=8 pins in accordance with embodiments of the present disclosure.
Figure 8C:
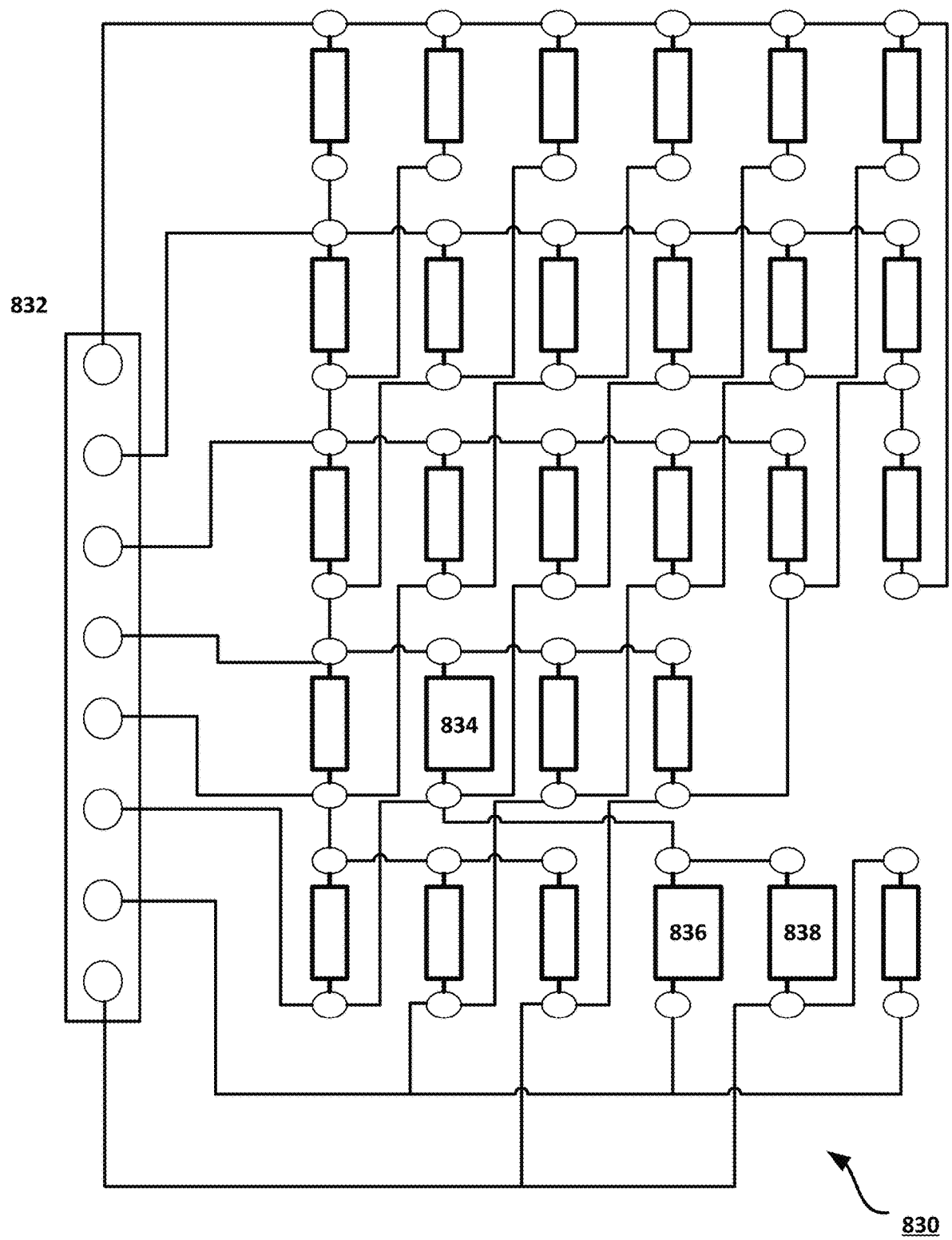
FIG. 8C is a schematic diagram of an example high-density analog multiplexer routing for N=8 pins optimized for an aspect ratio of approximately 1 in accordance with embodiments of the present disclosure.

FIGS. 8A-C illustrate placement, routing, and routing optimization for various load number implementation examples. FIG. 8A is a schematic diagram of an example high-density analog multiplexer (HDAM) 800 with routing for N=4 pins in accordance with embodiments of the present disclosure. HDAM 800 illustrates a source/sink element 802 that can include one or more source elements and one or more sink elements; each of source and sink elements 802 can be coupled to a load, represented by nodes 806 and impedance 804. Multiplexer 800 includes N=4 pins as source/sink and 6 impedance elements.

FIG. 8B is a schematic diagram of an example high-density analog multiplexer routing for N=8 pins in accordance with embodiments of the present disclosure. Multiplexer 820 includes N=8 source/sink pins 822 and (N(N−1))/2=28 supported impedance elements (represented as 824).

Placement of the sensor loads can be performed by a procedure that follows the pseudocode below (or something similar) using analog circuit design and layout techniques:

```
Placement pseudocode:
for source = 1: N − 1;
    for sink = source + 1 : N;
        load designator = source-sink;
        place on grid, row = source, column = sink.
```

The placement can be an initial placement of sensor loads without yet performing routing or routing optimization. Routing of the sensor loads can be performed by a procedure that follows the pseudocode below (or something similar):

```
Route layer 1:
For i = 1 : N;
    If source(netname) == i;
        Route connector(i) and netname;
Route layer 2:
For i = 1 : N;
    If sink(netname) == i;
        Route netname;
        Insert via if required;
```

The routing couples sensor loads to sources and sinks on a per layer basis. After placement of sensor loads and routing of sensor loads to sources and sinks, routing optimization can be performed. Routing optimization can provide efficient sensor data collection and reduce complexity of matrix solution equations or logic.

FIG. 8B is a schematic diagram of an example high-density analog multiplexer 830 routing for N=8 pins optimized for an aspect ratio of approximately 1 in accordance with embodiments of the present disclosure. HDAM 820 includes N=8 source/sink pins 832 and (N(N−1))/2=28 impedance elements. The placement, routing, and routing optimization is illustrated by HDAM 830 shown in FIG. 8C, where 8 pins and 28 impedance elements are placed in a different layout than shown in HDAM 820 shown FIG. 8B. By way of example, impedance element 834 can be coupled to a sink pin as well as to the source terminals of impedance elements 836 and 838 (shown as larger boxes for convenience).

Routing optimization of the sensor loads can be performed by a procedure that follows the pseudocode below (or something similar):

```
For finite number of times:
    select extreme load in first row;
    move to below diagonally;
    select extreme load in first column;
    move to above diagonally;
    Reroute;
    Check aspect ratio and save to buffer;
    Save corresponding changes of routing to buffer;
    If aspect ratio < min(buffer);
        Rerun loop for next extreme load;
    If aspect ratio > min(buffer);
        Undo;
```

Select min from buffer;
Apply corresponding routing changes.

The above pseudocode is representative of example process flows and algorithms for placement of sensor loads, routing, and routing optimization. Specific code can vary based on implementation choices.

Figure 9:
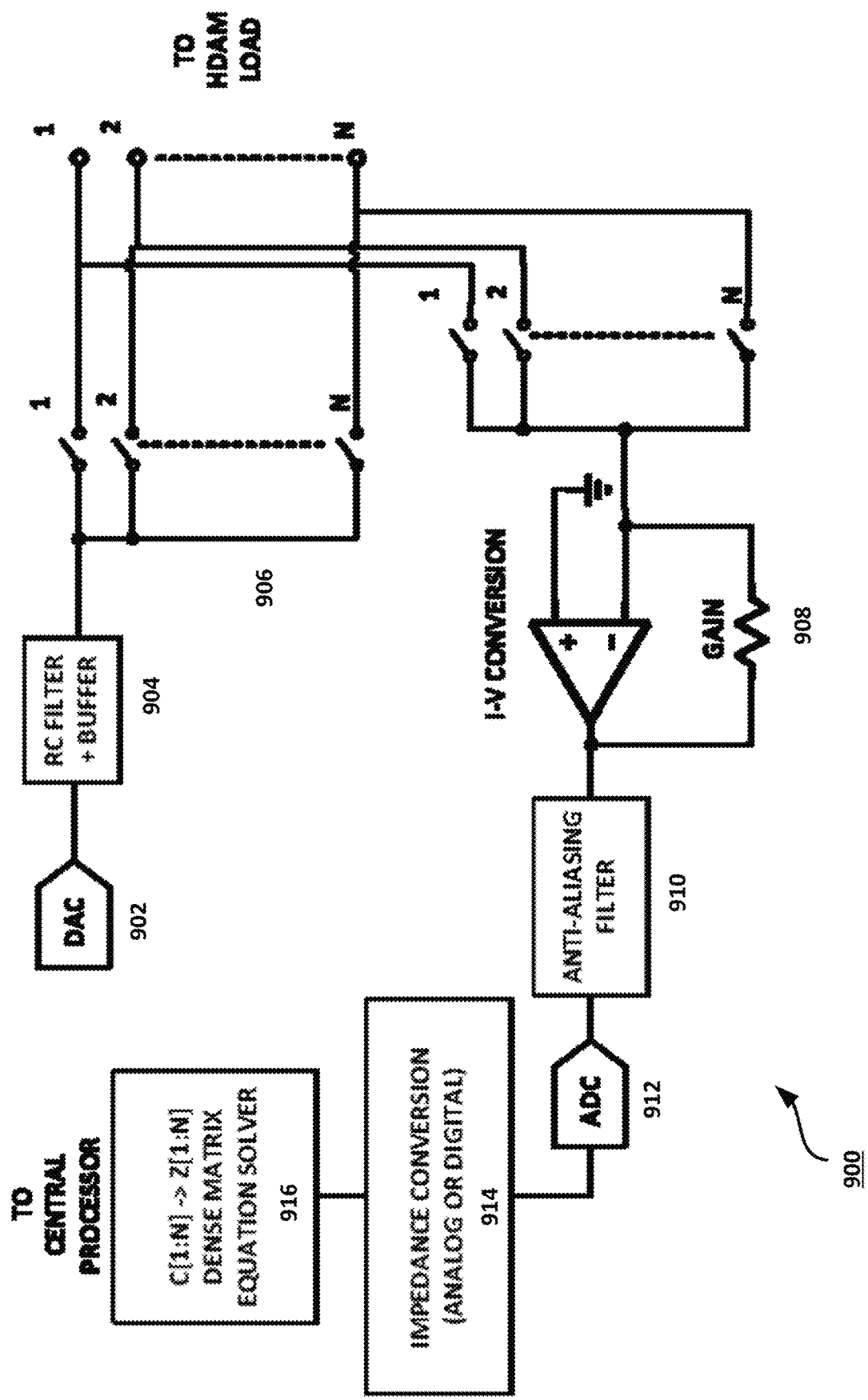
FIG. 9 is a schematic diagram of an example circuit level implementation of an N pin high-density analog multiplexer impedance sensor front-end in accordance with embodiments of the present disclosure.

FIG. 9 is a schematic diagram of an example circuit system 900 of an N pin high-density analog multiplexer impedance sensor front-end in accordance with embodiments of the present disclosure. An example tri-state I/O is illustrated as DAC 902, RC Filter+Buffer 904 and the switch network 906. Other implementations are also contemplated. The DAC 902 can provide an analog input to control the switch network to switch one or more outputs for HDAM sensor loads for multiplexer circuit(s). The tri-state I/O is also shown as the amplifier circuit element 908, which can include an operation amplifier or other gain circuit element. A dense matrix equation solver 916 can be used to resolve the values from the HDAM sensor loads to process the signal data. Dense matrix equation solver 916 can be implemented in hardware logic (e.g., digital logic), software, firmware, or a combination of hardware elements and software.

Other circuit elements can be used at the output of the multiplexer, such as an anti-aliasing logic 910, ADC 912, and an analog or digital impedance conversion logic 914. The anti-aliasing filter 910 can restrict signal bandwidth prior to sampling, to reduce noise. ADC 912 converts the analog output of the filtered HDAM into digital signals for processing. The impedance conversion logic 914 can provide impedance matching functionality for the circuit as a whole. Other circuit-level implementation choices can also be used.

Figure 10:
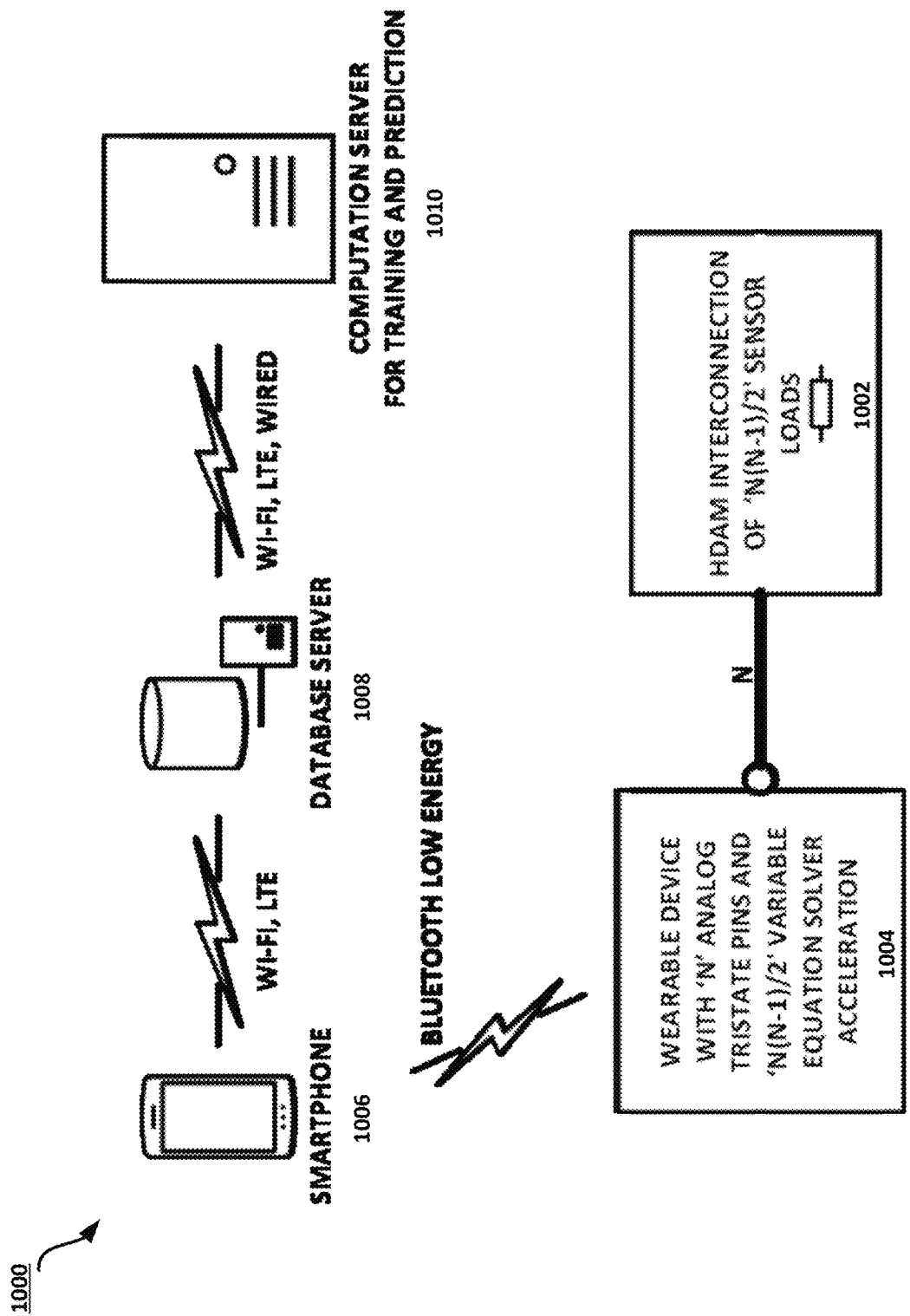
FIG. 10 is a schematic diagram of an example high-density analog multiplexer implementation in a wearable device ecosystem in accordance with embodiments of the present disclosure.

FIG. 10 is a schematic diagram of an example system 1000 that includes a high-density analog multiplexer implementation in a wearable device ecosystem in accordance with embodiments of the present disclosure. A wearable device 1004 can include the HDAM as described above, as well as the HDAM interconnection of (N(N−1))/2 sensor loads 1002. The wireless device can be a smartwatch, sporting watch, heartrate sensor, or other wearable device that includes a plurality of sensors. The wearable device 1004 can be connected to another computing platform by a wireless connection, such as a Bluetooth connection, cellular connection, Wi-fi connection, or other radio frequency communications protocol. The computing platform can be a smartphone, mobile device, laptop, tablet, desktop computer, remote server, or other computing platform that can receive wireless signals from the wearable device. The computing platform can communicate with other computing platforms using wired or wireless communications protocols.

Figure 11:
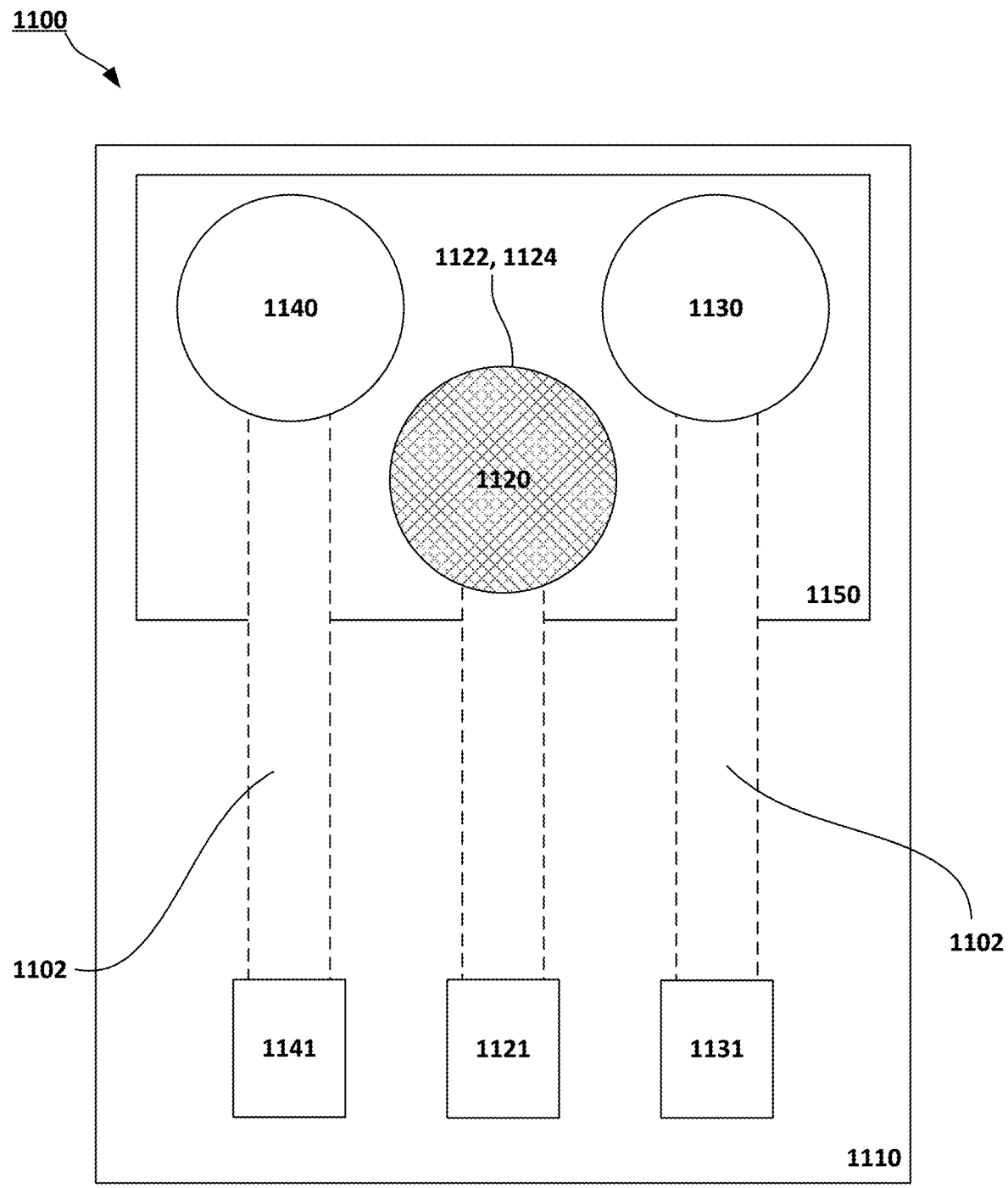
FIG. 11 is a schematic diagram of an example sensing device in accordance with some embodiments.

FIG. 11 shows a schematic of a sensing device 1100 in accordance with some embodiments. The sensing device 1100 may be used to conduct one or more immunoassays for detecting one or more target analytes in a sample. The sensing device may contain a plurality of capture reagents for conducting the one or more immunoassays. The capture reagents may be disposed or immobilized on a surface of at least one electrode of the sensing device. Generally, the sensing device comprises materials suitable for performing biosensing, by providing appropriate materials for immobilizing or otherwise providing various capture reagents to perform the immunoassay.

Referring to FIG. 11, the sensing device 1100 may comprise a substrate 1110. The substrate may be flexible or rigid. The substrate may include materials such as polyimide, silicon, glass, printed circuit boards (PCB), polyurethane, polycarbonate, polyamide, or the like. In some embodiments, the substrate may be an organic substrate comprising flexible PCB materials. In some embodiments, the substrate may be a flexible and porous polyimide substrate that allows very low volumes of fluid adsorption within its pores, which in turn facilitates more effective conjugation and thus improved sensitivity in the detection of one or more target analytes present in the fluid sample. In some embodiments, the substrate may be capable of flexing or bending a large number of cycles without substantially impacting the accuracy and sensitivity of the sensing device.

In some embodiments, the substrate may include test strips for aiding lateral transport of a sample fluid to electrodes on the sensing device. Non-limiting examples of test strips may include porous paper, or a membrane polymer such as nitrocellulose, polyvinylidene fluoride, nylon, Fusion 5™, or polyethersulfone.

In some embodiments, the sensing device may be provided on a single electrochemical test strip. For example, the sensing device need not include multiple electrochemical test strips for performing the simultaneous and multiplexed detection of a plurality of target analytes.

The sensing device 1100 may comprise two or more electrodes disposed on the substrate. For example, in the embodiment shown in FIG. 11, a working electrode (WE) 1120, a reference electrode (RE) 1130, and a counter electrode (CE) 1140 may be disposed on the substrate 1110. Any number or type of electrodes may be contemplated. The electrodes may be exposed to a sample suspected to contain one or more target analytes. A working electrode (WE) as described anywhere herein may be referred to interchangeably as a sensing electrode, a sensing working electrode, detection electrode, or the like. The WE 1120 may comprise a conducting electrode stack. The WE 1120 may further comprise a semiconducting sensing element (e.g., a plurality of semiconducting nanostructures 1122) formed on its surface, as described in detail elsewhere herein. The RE 1130 and CE 1140 may each comprise a conducting electrode stack, and need not comprise sensing elements on their surfaces. For example, the RE 130 and CE 140 need not include molecules that are used for functionalizing the sensing element on the WE 1120. The CE 1140 and RE 1130 may be electrochemically inert/stable, and may collectively form an electrochemical cell with the WE 1120 when the electrodes come into contact with the fluid sample (electrolyte or ionic liquid).

The electrodes may be formed of various shapes and/or sizes. The electrodes may have a substantially circular or oval shape, for example as shown in FIG. 11. In some embodiments, the electrodes may have a regular shape (e.g. polygonal shapes such as triangular, pentagonal, hexagonal, etc.) or an irregular shape. The electrodes may be of the same size or different sizes. The electrodes may have the surface areas or different surface areas. The ratio of the surface areas of WE:CE:RE may be given by x:y:z, where x, y and z may be any integer. In some instances, z may be larger than x and y, such that the RE 1130 has a larger surface area than each of WE 1120 and CE 1140. For example, the ratio of the surface areas of WE:CE:RE may be 1:1:2, 1:1:3, 1:1:4, 1:1:5, 1:1:6, or any other ratio. In some preferred embodiments, the ratio of the surface areas of WE:CE:RE may be 1:1:4, but is not limited thereto.

The electrodes on the sensing device 1100 may be electrically connected to a plurality of contact pads via conducting layer traces 1102 embedded or formed on the substrate. Each electrode may be connected to a contact pad. For example, the working electrode 1120 may be connected to a first contact pad 1121, the reference electrode 1130 may be connected to a second contact pad 1131, and the counter electrode 1140 may be connected to a third contact pad 1141. In some alternative embodiments, two or more electrodes may be connected to a contact pad. Optionally, an electrode may be connected to two or more contact pads. The contact pads may be located at a distance from the electrodes. In some embodiments, the contact pads and electrodes may be located at opposite ends of the substrate. The contact pads may be provided on a same surface of the substrate 1110 as the electrodes. Alternatively, the contact pads may be provided on a different surface of the substrate 1110 as the electrodes. For example, the contact pads and the electrodes may be provided on opposite surfaces of the substrate.

The conducting layer traces 1102 may be formed of a metal, e.g. Cu. The electrodes 1120, 1130, and 1140 may include a surface finish formed on the conducting layer traces. Non-limiting examples of surface finishes may include electroless nickel deposited on a copper trace, or an immersion gold/immersion silver/electrolytic gold deposited on an electroless nickel surface.

In some embodiments, different surface finishes on a flexible printed circuit board substrate may comprise the following exemplary thickness ranges: (1) For Immersion Silver, 8-15 micro-inches of 99% pure silver over Cu trace layer with good surface planarity, which may be a preferred surface finish for RE 1130. In some cases, the post immersion silver surface finish may be chemically modified to form an Ag/AgCl surface that offers excellent electrochemical stability. (2) For Electroless Nickel Immersion Gold (ENIG), 2-8 micro-inches Au layer over 120-240 micro-inches electroless Ni layer over Cu trace layer. (3) For Electroless Nickel Electroless Palladium Immersion Gold (ENEPIG), 2-8 micro-inches Au layer over 4-20 micro-inches electroless Pd layer over 120-240 micro-inches electroless Ni layer. The Pd layer can eliminate corrosion potential from immersion reaction. Au surfaces are relatively stable/inert, offer wide electrochemical window and can be used for the WE 1120 and CE 1140. It should be appreciated that the above thickness values are merely exemplary, and that different thickness values may be contemplated for different surface finishes depending on the desired electrical and sensing properties.

Semiconducting nanostructures may be disposed on at least one of the electrodes to aid in sensing of one or more target analytes. For example, a sensing element comprising a layer of semiconducting nanostructures 1122 may be deposited over the surface of the WE 1120. The WE 1120 may include one or more of the surface finishes described herein. The choice of semiconducting nanostructures 1122 may be determined based on the catalytic properties of the semiconducting material. In some embodiments, metal oxide nanostructured surfaces can offer immobilization when selectively functionalized with thiol and phosphonic acid linker chemistries to form specific interactions with the protein biomolecules, that can lead to enhancements in specific output signal response and enhanced specificity in biomarker detection.

Non-limiting examples of semiconducting materials that can be used on a working electrode may include the following: Diamond, Silicon, Germanium, Gray tin (α-Sn), Sulfur (α-S), Gray selenium, Tellurium, Silicon carbide (3C—SiC), Silicon carbide (4H—SiC), Silicon carbide (6H—SiC), Boron nitride (cubic), Boron nitride (hexagonal), Boron nitride (nanotube), Boron phosphide, Boron arsenide, Aluminium nitride, Aluminium phosphide, Aluminium arsenide, Aluminium antimonide, Gallium nitride, Gallium phosphide, Gallium, arsenide, Gallium antimonide, Indium nitride, Indium, phosphide, Indium arsenide, Indium antimonide, Cadmium selenide, Cadmium, sulfide, Cadmium telluride, Zinc oxide, Zinc selenide, Zinc sulfide, Zinc telluride, Cuprous, chloride, Copper sulfide, Lead selenide, Lead(II) sulfide, Lead telluride, Tin sulfide, Tin sulfide, Tin telluride, Bismuth, telluride, Cadmium phosphide, Cadmium arsenide, Cadmium antimonide, Zinc phosphide, Zinc arsenide, Zinc antimonide, Titanium dioxide (anatase), Titanium dioxide (rutile), Titanium dioxide (brookite), Copper (I) oxide, Copper(II) oxide, Uranium, dioxide, Uranium, trioxide, Bismuth, trioxide, Tin dioxide, Lead(II) iodide, Molybdenum disulfide, Gallium, selenide, Tin sulfide, Bismuth sulfide, Iron(II) oxide, Nickel(II) oxide, Europium(II) oxide, Europium(II) sulfide, Chromium(III) bromide, Arsenic sulfideOrpiment, Arsenic sulfideRealgar, Platinum, silicide, Bismuth(III) iodide, Mercury(II) iodide, Thallium(I) bromide, Silver sulfide, Iron disulfide, Lead tin, telluride, Thallium tin telluride, Thallium germanium telluride, Barium titanate, Strontium, titanate, Lithium niobate, Lanthanum copper oxide, Gallium manganese arsenide, Indium manganese arsenide, Cadmium manganese telluride, Lead manganese telluride, Copper indium selenide (CIS), Silver gallium sulfide, Zinc silicon phosphide, Copper tin sulfide (CTS), Lanthanum calcium manganite, Copper zinc tin sulfide (CZTS), or Copper zinc antimony sulfide (CZAS).

Non-limiting examples of semiconductor alloy materials that can be used on a working electrode may include the following: Silicon-germanium, Silicon-tin, Aluminium gallium arsenide, Indium gallium arsenide, Indium gallium phosphide, Aluminium indium arsenide, Aluminium indium antimonide, Gallium arsenide nitride, Gallium arsenide phosphide, Gallium arsenide antimonide, Aluminium gallium nitride, Aluminium gallium phosphide, Indium gallium nitride, Indium arsenide antimonide, Indium gallium antimonide, Cadmium zinc telluride (CZT), Mercury cadmium telluride, Mercury zinc telluride, Mercury zinc selenide, Aluminium gallium indium phosphide, Aluminium gallium arsenide phosphide, Indium gallium arsenide phosphide, Indium gallium arsenide antimonide, Indium arsenide antimonide phosphide, Aluminium indium arsenide phosphide, Aluminium gallium arsenide nitride Indium gallium arsenide nitride, Indium aluminium arsenide nitride, Gallium arsenide antimonide nitride, Copper indium gallium selenide (CIGS), Gallium indium nitride arsenide antimonide, or Gallium indium arsenide antimonide phosphide.

In some preferred embodiments, the plurality of semiconducting nanostructures 1122 may comprise ZnO. ZnO is suitable for detecting biomolecules for a wide range of disease biomarkers due to its multifunctional characteristics and ability to form anisotropic nanostructures. The properties of ZnO such as good biocompatibility, wide band gap, non-toxicity, fast electron transfer, high isoelectricpoint (IEP: 9.5), favorable surface for linker chemistry binding, ease in formation of highly c-axis oriented nanostructures at low temperatures (<100° C.) and on various substrates including flexible polymeric substrates, and heightened sensitivity to adsorbed molecules render ZnO an attractive material of choice for affinity sensing applications and with both direct current (DC) and alternating current (AC) electrochemical methods. ZnO is preferred for designing sensors based on electrical transduction. Furthermore, ZnO with its single crystalline state is advantageous in the integration with flexible polymeric substrates, and offers low-cost of ownership manufacturing processes.

It is noted that any semiconducting materials with appropriate functionalization can be utilized on the working electrode(s) of the sensing device. In some embodiments, the metal oxide thin films and nanostructures of ZnO, TiO2, CNT-TiO2, SnO2, ZrO2, etc. can be used for design of glucose oxide, cholesterol oxidase and other enzymatic sensing devices. For catalytic based sensing devices, the choice of metal/semiconductor (examples: Ag, Au, Pd, Ni, Zn, Co, W, Mo, Mn, and their respective alloys such as ZnO, TiO2, MnO2, MoS2, etc.) as the sensing electrode material may also be dependent on the electrocatalytic properties of the material and the stability of the material at the temperature of operation of the sensor, the pH range of the buffer solution containing the target analytes, and the electrochemical potential window for the detection of the target analytes.

In some embodiments, the plurality of semiconducting nanostructures 1122 may be thermally grown on the working electrode in a configuration that aids in radial diffusion of the sample around the plurality of semiconducting nanostructures.

A plurality of capture reagents 1124 may be attached to the plurality of semiconducting nanostructures 1122 on the surface of the working electrode 1120. The plurality of capture reagents are configured to selectively bind to one or more target analytes in a fluid sample, thereby effecting changes to electron and ion mobility and charge accumulation in different regions of the semiconducting nanostructures and the fluid sample. The changes to the electron and ion mobility and charge accumulation are detectable with aid of sensing circuitry, and can be used to determine a presence and concentration of the one or more target analytes in the fluid sample.

The capture reagents 1124 may include an antibody or antibody fragment, an antigen, an aptamer, a peptide, a small molecule, a ligand, a molecular complex or any combination thereof. Essentially, the capture reagents may be any reagents that have specific binding activity for different target analytes. In some cases, a first capture reagent and a second capture reagent may be antibodies or antibody fragments that specifically bind to epitopes present on a first target analyte and a second target analyte, respectively. Immunoglobulin molecules can be of any type (e.g., IgG, IgE, IgM, IgD, IgA and IgY), class (e.g., IgG1, IgG2, IgG3, IgG4, IgA1 and IgA2) or subclass of immunoglobulin molecule. In some cases, the antibody is an antigen-binding antibody fragment such as, for example, a Fab, a F(ab'), a F(ab')2, a Fd chain, a single-chain Fv (scFv), a single-chain antibody, a disulfide-linked Fv (sdFv), a fragment comprising either a VL or VH domain, or fragments produced by a Fab expression library. Antigen-binding antibody fragments, including single-chain antibodies, can comprise the variable region(s) alone or in combination with the entirety or a portion of the following: hinge region, CH1, CH2, CH3 and CL domains. Also, antigen-binding fragments can comprise any combination of variable region(s) with a hinge region, CH1, CH2, CH3 and CL domains. Antibodies and antibody fragments may be derived from a human, rodent (e.g., mouse and rat), donkey, sheep, rabbit, goat, guinea pig, camelid, horse, or chicken. Various antibodies and antibody fragments may be designed to selectively bind essentially any desired analyte. Methods of generating antibodies and antibody fragments are well known in the art.

The terms "selective" or "specific" binding may be used herein interchangeably. Generally speaking, a ligand that selectively or specifically binds to a target means that the ligand has a high binding affinity for its target, and a low binding affinity for non-target molecules. The dissociation constant (Kd) may be used herein to describe the binding affinity of a ligand for a target molecule (e.g., an analyte). The dissociation constant may be defined as the molar concentration at which half of the binding sites of a target molecule are occupied by the ligand. Therefore, the smaller the Kd, the tighter the binding of the ligand to the target molecule. In some cases, a ligand has a dissociation constant (Kd) for a target molecule of less than 1 mM, less than 100 ⍰M, less than 10 ⍰M, less than 1 ⍰M, less than 100 nM, less than 50 nM, less than 25 nM, less than 10 nM, less than 5 nM, less than 1 nM, less than 500 μM, less than 100 μM, less than 50 μM, or less than 5 μM.

The plurality of semiconducting nanostructures may comprise surfaces that are functionalized with a linking reagent. The capture reagents may be immobilized onto the surfaces of the semiconducting nanostructures via the linking reagent.

The sensing device is capable of determining the presence and concentration of one or more target analytes in a sample, without the use of any visual markers or labels conjugated to the capture reagents. In various embodiments, the capture detection reagents need not be conjugated or otherwise attached to a detectable label. A detectable label may be a fluorophore, an enzyme, a quencher, an enzyme inhibitor, a radioactive label, one member of a binding pair or any combination thereof. In contrast, other known protein sensing devices often require a label attached to the target protein for detection and quantification. Labeling a biomolecule can drastically change its binding properties, and the yield of the target-label coupling reaction can be highly variable which may affect the detection of protein targets.

The sensing device disclosed herein can circumvent the issues associated with labeling, by using label-free methods for protein detection. Many protein sensors are affinity-based which uses an immobilized capture reagent that binds a target biomolecule. The challenge of detecting a target analyte in solution lies in detecting changes at a localized surface. The use of nanomaterials (e.g. semiconducting nanostructures) as capture surfaces can be particularly beneficial when designing ultra-sensitive electrical sensing devices that rely on measured current and/or voltage to detect binding events. Electrical sensing techniques, such as the modified electrochemical impedance spectroscopy (EIS) technique described herein, have the ability to rapidly detect protein biomarkers at low concentrations. Impedance measurements can be especially useful since they do not require special labels and are therefore suitable for label-free capture operation.

Referring to FIG. 11, the substrate 1110 may include a test zone 1150 for receiving a sample. The test zone may correspond to a portion or region of the sensing device that is configured to receive or accept a sample. The test zone may be located anywhere on the sensing device, for example at or near an end portion of the substrate. A sample may be applied to the test zone by, e.g., inserting the end portion of the device containing the test zone into a container holding the sample, by pipetting a fluid sample directly onto the test zone, or by holding the test zone of the device under a fluid stream. Generally, the sample is a fluid sample. In other cases, the sample is a solid sample that is modified to form a fluid sample, for example, dissolved or disrupted (e.g., lysed) in a liquid medium.

In some embodiments, a test zone may optionally include a pad or other contact surface. In some cases, the pad may be composed of a woven mesh or a fibrous material such as a cellulose filter, polyesters, or glass fiber. The test zone may further include, without limitation, pH and ionic strength modifiers such as buffer salts (e.g., Tris), viscosity enhancers to modulate flow properties, blocking and resolubilization agents (e.g., proteins (such as albumin), detergents, surfactants (such as Triton X-100, Tween-20), and/or filtering agents (e.g., for whole blood)).

Generally, the sample applied to the test zone 1150 may be a fluid sample or a solid sample modified with a liquid medium. In various aspects, the sample is a biological sample. Non-limiting examples of biological samples suitable for use with the immunoassay devices of the disclosure include: whole blood, blood serum, blood plasma, urine, feces, saliva, vaginal secretions, semen, interstitial fluid, mucus, sebum, sweat, tears, crevicular fluid, aqueous humor, vitreous humor, bile, breast milk, cerebrospinal fluid, cerumen, enolymph, perilymph, gastric juice, peritoneal fluid, vomit, and the like. The biological sample can be obtained from a hospital, laboratory, clinical or medical laboratory. In some cases, the immunoassay test using the sensing device is performed by a clinician or laboratory technician. In other cases, the immunoassay test using the sensing device is performed by the subject, for example, at home.

The biological sample can be from a subject, e.g., a plant, fungi, eubacteria, archaebacteria, protist, or animal. The subject can be an organism, either a single-celled or multicellular organism. The subject can be cultured cells, which can be primary cells or cells from an established cell line, among others. Examples of cell lines include, but are not limited to, 293-T human kidney cells, A2870 human ovary cells, A431 human epithelium, B35 rat neuroblastoma cells, BHK-21 hamster kidney cells, BR293 human breast cells, CHO Chinese hamster ovary cells, CORL23 human lung cells, HeLa cells, or Jurkat cells. The sample can be isolated initially from a multi-cellular organism in any suitable form. The animal can be a fish, e.g., a zebrafish. The animal can be a mammal. The mammal can be, e.g., a dog, cat, horse, cow, mouse, rat, or pig. The mammal can be a primate, e.g., a human, chimpanzee, orangutan, or gorilla. The human can be a male or female. The sample can be from a human embryo or human fetus. The human can be an infant, child, teenager, adult, or elderly person. The female can be pregnant, suspected of being pregnant, or planning to become pregnant. The female can be ovulating. In some cases, the sample is a single or individual cell from a subject and the biological sample is derived from the single or individual cell. In some cases, the sample is an individual micro-organism, or a population of micro-organisms, or a mixture of micro-organisms and host cells.

In some cases, the biological sample comprises one or more bacterial cells. In some cases, the one or more bacterial cells are pathogens. In some cases, the one or more bacterial cells are infectious. Non-limiting examples of bacterial pathogens that can be detected include Mycobacteria (e.g. *M. tuberculosis, M. bovis, M. avium, M. leprae*, and *M. africanum*), rickettsia, mycoplasma, chlamydia, and legionella. Some examples of bacterial infections include, but are not limited to, infections caused by Gram positive *bacillus* (e.g., *Listeria, Bacillus* such as *Bacillus anthracia, Erysipelothrix* species), Gram negative *bacillus* (e.g., *Bartonella, Brucella, Campylobacter, Enterobacter, Escherichia, Francisella, Hemophilus, Klebsiella, Morganella, Proteus, Providencia, Pseudomonas, Salmonella, Serratia, Shigella, Vibrio* and *Yersinia* species), spirochete bacteria (e.g., *Borrelia* species including *Borrelia burgdorferi* that causes Lyme disease), anaerobic bacteria (e.g., *Actinomyces* and *Clostridium* species), Gram positive and negative coccal bacteria, *Enterococcus* species, *Streptococcus* species, *Pneumococcus* species, *Staphylococcus* species, and *Neisseria* species. Specific examples of infectious bacteria include, but are not limited to: *Helicobacter pyloris, Legionella pneumophilia, Mycobacterium tuberculosis, Mycobacterium avium, Mycobacterium intracellulare, Mycobacterium kansaii, Mycobacterium gordonae, Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus viridans, Streptococcus faecalis, Streptococcus bovis, Streptococcus pneumoniae, Haemophilus influenzae, Bacillus antracis, Erysipelothrix rhusiopathiae, Clostridium tetani, Enterobacter aerogenes, Klebsiella pneumoniae, Pasturella multocida, Fusobacterium nucleatum, Streptobacillus moniliformis, Treponema pallidum, Treponema pertenue, Leptospira, Rickettsia*, and *Actinomyces israelii, Acinetobacter, Bacillus, Bordetella, Borrelia, Brucella, Campylobacter, Chlamydia, Chlamydophila, Clostridium, Corynebacterium, Enterococcus, Haemophilus, Helicobacter, Mycobacterium, Mycoplasma, Stenotrophomonas, Treponema, Vibrio, Yersinia, Acinetobacter baumanii, Bordetella pertussis, Brucella abortus, Brucella canis, Brucella melitensis, Brucella suis, Campylobacter jejuni, Chlamydia pneumoniae, Chlamydia trachomatis, Chlamydophila psittaci, Clostridium botulinum, Clostridium difficile, Clostridium perfringens, Corynebacterium diphtheriae, Enterobacter sazakii, Enterobacter agglomerans, Enterobacter cloacae, Enterococcus faecalis, Enterococcus faecium, Escherichia coli, Francisella tularensis, Helicobacter pylori, Legionella pneumophila, Leptospira interrogans, Mycobacterium leprae, Mycobacterium tuberculosis, Mycobacterium ulcerans, Mycoplasma pneumoniae, Pseudomonas aeruginosa, Rickettsia rickettsii, Salmonella typhi, Salmonella typhimurium, Salmonella enterica, Shigella sonnei, Staphylococcus epidermidis, Staphylococcus saprophyticus, Stenotrophomonas maltophilia, Vibrio cholerae, Yersinia pestis*, and the like.

The biological sample may comprise one or more viruses. Non-limiting examples of viruses include the herpes virus (e.g., human cytomegalomous virus (HCMV), herpes simplex virus 1 (HSV-1), herpes simplex virus 2 (HSV-2), varicella zoster virus (VZV), Epstein-Barr virus), influenza A virus and Hepatitis C virus (HCV) or a picornavirus such as Coxsackievirus B3 (CVB3). Other viruses may include, but are not limited to, the hepatitis B virus, HIV, poxvirus, hepadavirus, retrovirus, and RNA viruses such as flavivirus, togavirus, coronavirus, Hepatitis D virus, orthomyxovirus, paramyxovirus, rhabdovirus, bunyavirus, filo virus, Adenovirus, Human herpesvirus, type 8, Human papillomavirus, BK virus, JC virus, Smallpox, Hepatitis B virus, Human bocavirus, Parvovirus B19, Human astrovirus, Norwalk virus, coxsackievirus, hepatitis A virus, poliovirus, rhinovirus, Severe acute respiratory syndrome virus, Hepatitis C virus, yellow fever virus, dengue virus, West Nile virus, Rubella virus, Hepatitis E virus, and Human immunodeficiency virus (HIV). In some cases, the virus is an enveloped virus. Examples include, but are not limited to, viruses that are members of the hepadnavirus family, herpesvirus family, iridovirus family, poxvirus family, flavivirus family, togavirus family, retrovirus family, coronavirus family, filovirus family, rhabdovirus family, bunyavirus family, orthomyxovirus family, paramyxovirus family, and arenavirus family. Other examples include, but are not limited to, Hepadnavirus hepatitis B virus (HBV), woodchuck hepatitis virus, ground squirrel (Hepadnaviridae) hepatitis virus, duck hepatitis B virus, heron hepatitis B virus, Herpesvirus herpes simplex virus (HSV) types 1 and 2, varicella-zoster virus, cytomegalovirus (CMV), human cytomegalovirus (HCMV), mouse cytomegalovirus (MCMV), guinea pig cytomegalovirus (GPCMV), Epstein-Barr virus (EBV), human herpes virus 6 (HHV variants A and B), human herpes virus 7 (HHV-7), human herpes virus 8 (HHV-8), Kaposi's sarcoma—associated herpes virus (KSHV), B virus Poxvirus vaccinia virus, variola virus, smallpox virus, monkeypox virus, cowpox virus, camelpox virus, ectromelia virus, mousepox virus, rabbitpox viruses, raccoonpox viruses, molluscum contagiosum virus, orf virus, milker's nodes virus, bovin papullar stomatitis virus, sheeppox virus, goatpox virus, lumpy skin disease virus, fowlpox virus, canarypox virus, pigeonpox virus, sparrowpox virus, myxoma virus, hare fibroma virus, rabbit fibroma virus, squirrel fibroma viruses, swinepox virus, tanapox virus, Yabapox virus, Flavivirus dengue virus, hepatitis C virus (HCV), GB hepatitis viruses (GBV-A, GBV-B and GBV-C), West Nile virus, yellow fever virus, St. Louis encephalitis virus, Japanese encephalitis virus, Powassan virus, tick-borne encephalitis virus, Kyasanur Forest disease virus, Togavirus, Venezuelan equine encephalitis (VEE) virus, chikungunya virus, Ross River virus, Mayaro virus, Sindbis virus, rubella virus, Retrovirus human immunodeficiency virus (HIV) types 1 and 2, human T cell leukemia virus (HTLV) types 1, 2, and 5, mouse mammary tumor virus (MMTV), Rous sarcoma virus (RSV), lentiviruses, Coronavirus, severe acute respiratory syndrome (SARS) virus, Filovirus Ebola virus, Marburg virus, Metapneumoviruses (MPV) such as human metapneumovirus (HMPV), Rhabdovirus rabies virus, vesicular stomatitis virus, Bunyavirus, Crimean-Congo hemorrhagic fever virus, Rift Valley fever virus, La Crosse virus, Hantaan virus, Orthomyxovirus, influenza virus (types A, B, and C), Paramyxovirus, parainfluenza virus (PIV types 1, 2 and 3), respiratory syncytial virus (types A and B), measles virus, mumps virus, Arenavirus, lymphocytic choriomeningitis virus, Junin virus, Machupo virus, Guanarito virus, Lassa virus, Ampari virus, Flexal virus, Ippy virus, Mobala virus, Mopeia virus, Latino virus, Parana virus, Pichinde virus, Punta toro virus (PTV), Tacaribe virus and Tamiami virus. In some embodiments, the virus is a non-enveloped virus, examples of which include, but are not limited to, viruses that are members of the parvovirus family, circovirus family, polyoma virus family, papillomavirus family, adenovirus family, iridovirus family, reovirus family, birnavirus family, calicivirus family, and picornavirus family. Specific examples include, but are not limited to, canine parvovirus, parvovirus B19, porcine circovirus type 1 and 2, BFDV (Beak and Feather Disease virus, chicken anaemia virus, Polyomavirus, simian virus 40 (SV40), JC virus, BK virus, Budgerigar fledgling disease virus, human papillomavirus, bovine papillomavirus (BPV) type 1, cotton tail rabbit papillomavirus, human adenovirus (HAdV-A, HAdV-B, HAdV-C, HAdV-D, HAdV-E, and HAdV-F), fowl adenovirus A, bovine adenovirus D, frog adenovirus, Reovirus, human orbivirus, human coltivirus, mammalian orthoreovirus, bluetongue virus, rotavirus A, rotaviruses (groups B to G), Colorado tick fever virus, aquareovirus A, cypovirus 1, Fiji disease virus, rice dwarf virus, rice ragged stunt virus, idnoreovirus 1, mycoreovirus 1, Birnavirus, bursal disease virus, pancreatic necrosis virus, Calicivirus, swine vesicular exanthema virus, rabbit hemorrhagic disease virus, Norwalk virus, Sapporo virus, Picornavirus, human polioviruses (1-3), human coxsackieviruses Al-22, 24 (CAI-22 and CA24, CA23 (echovirus 9)), human coxsackieviruses (BI-6 (CBI-6)), human echoviruses 1-7, 9, 11-27, 29-33, vilyuish virus, simian enteroviruses 1-18 (SEV1-18), porcine enteroviruses 1-11 (PEVI-11), bovine enteroviruses 1-2 (BEV1-2), hepatitis A virus, rhinoviruses, hepatoviruses, cardio viruses, aphthoviruses and echoviruses. The virus may be phage. Examples of phages include, but are not limited to T4, T5, λ phage, T7 phage, G4, P1, ϕ6, *Thermoproteus term* virus 1, M13, MS2, Qβ, ϕX174, Φ29, PZA, Φ15, BS32, B103, M2Y (M2), Nf, GA-1, FWLBc1, FWLBc2, FWLLm3, B4. In some cases, the virus is selected from a member of the Flaviviridae family (e.g., a member of the Flavivirus, Pestivirus, and Hepacivirus genera), which includes the hepatitis C virus, Yellow fever virus; Tick-borne viruses, such as the Gadgets Gully virus, Kadam virus, Kyasanur Forest disease virus, Langat virus, Omsk hemorrhagic fever virus, Powassan virus, Royal Farm virus, Karshi virus, tick-borne encephalitis virus, Neudoerfl virus, Sofjin virus, Louping ill virus and the Negishi virus; seabird tick-borne viruses, such as the Meaban virus, Saumarez Reef virus, and the Tyuleniy virus; mosquito-borne viruses, such as the Aroa virus, dengue virus, Kedougou virus, Cacipacore virus, Koutango virus, Japanese encephalitis virus, Murray Valley encephalitis virus, St. Louis encephalitis virus, Usutu virus, West Nile virus, Yaounde virus, Kokobera virus, Bagaza virus, Ilheus virus, Israel turkey meningoencephalomyelitis virus, Ntaya virus, Tembusu virus, Zika virus, Banzi virus, Bouboui virus, Edge Hill virus, Jugra virus, Saboya virus, Sepik virus, Uganda S virus, Wesselsbron virus, yellow fever virus; and viruses with no known arthropod vector, such as the Entebbe bat virus, Yokose virus, Apoi virus, Cowbone Ridge virus, Jutiapa virus, Modoc virus, Sal Vieja virus, San Perlita virus, Bukalasa bat virus, Carey Island virus, Dakar bat virus, Montana myotic leukoencephalitis virus, Phnom Penh bat virus, Rio Bravo virus, Tamana bat virus, and the Cell fusing agent virus. In some cases, the virus is selected from a member of the Arenaviridae family, which includes the Ippy virus, Lassa virus (e.g., the Josiah, LP, or GA391 strain), lymphocytic choriomeningitis virus (LCMV), Mobala virus, Mopeia virus, Amapari virus, Flexal virus, Guanarito virus, Junin virus, Latino virus, Machupo virus, Oliveros virus, Parana virus, Pichinde virus, Pirital virus, Sabia virus, Tacaribe virus, Tamiami virus, Whitewater Arroyo virus, Chapare virus, and Lujo virus. In some cases, the virus is selected from a member of the Bunyaviridae family (e.g., a member of the Hantavirus, Nairovirus, Orthobunyavirus, and Phlebovirus genera), which includes the Hantaan virus, Sin Nombre virus, Dugbe virus, Bunyamwera virus, Rift Valley fever virus, La Crosse virus, Punta Toro virus (PTV), California encephalitis virus, and Crimean-Congo hemorrhagic fever (CCHF) virus. In some cases, the virus is selected from a member of the Filoviridae family, which includes the Ebola virus (e.g., the Zaire, Sudan, Ivory Coast, Reston, and Uganda strains) and the Marburg virus (e.g., the Angola, Ci67, Musoke, Popp, Ravn and Lake Victoria strains); a member of the Togaviridae family (e.g., a member of the Alphavirus genus), which includes the Venezuelan equine encephalitis virus (VEE), Eastern equine encephalitis virus (EEE), Western equine encephalitis virus (WEE), Sindbis virus, rubella virus, Semliki Forest virus, Ross River virus, Barmah Forest virus, O' nyong'nyong virus, and the chikungunya virus; a member of the Poxyiridae family (e.g., a member of the Orthopoxvirus genus), which includes the smallpox virus, monkeypox virus, and vaccinia virus; a member of the Herpesviridae family, which includes the herpes simplex virus (HSV; types 1, 2, and 6), human herpes virus (e.g., types 7 and 8), cytomegalovirus (CMV), Epstein-Barr virus (EBV), Varicella-Zoster virus, and Kaposi's sarcoma associated-herpesvirus (KSHV); a member of the Orthomyxoviridae family, which includes the influenza virus (A, B, and C), such as the H5N1 avian influenza virus or H1N1 swine flu; a member of the Coronaviridae family, which includes the severe acute respiratory syndrome (SARS) virus; a member of the Rhabdoviridae family, which includes the rabies virus and vesicular stomatitis virus (VSV); a member of the Paramyxoviridae family, which includes the human respiratory syncytial virus (RSV), Newcastle disease virus, hendravirus, nipahvirus, measles virus, rinderpest virus, canine distemper virus, Sendai virus, human parainfluenza virus (e.g., 1, 2, 3, and 4), rhinovirus, and mumps virus; a member of the Picornaviridae family, which includes the poliovirus, human enterovirus (A, B, C, and D), hepatitis A virus, and the coxsackievirus; a member of the Hepadnaviridae family, which includes the hepatitis B virus; a member of the Papillamoviridae family, which includes the human papilloma virus; a member of the Parvoviridae family, which includes the adeno-associated virus; a member of the Astroviridae family, which includes the astrovirus; a member of the Polyomaviridae family, which includes the JC virus, BK virus, and SV40 virus; a member of the Calciviridae family, which includes the Norwalk virus; a member of the Reoviridae family, which includes the rotavirus; and a member of the Retroviridae family, which includes the human immunodeficiency virus (HIV; e.g., types 1 and 2), and human T-lymphotropic virus Types I and II (HTLV-1 and HTLV-2, respectively).

The biological sample may comprise one or more fungi. Examples of infectious fungal agents include, without limitation *Aspergillus, Blastomyces, Coccidioides, Cryptococcus, Histoplasma, Paracoccidioides, Sporothrix*, and at least three genera of *Zygomycetes*. The above fungi, as well as many other fungi, can cause disease in pets and companion animals. The present teaching is inclusive of substrates that contact animals directly or indirectly. Examples of organisms that cause disease in animals include *Malassezia furfur, Epidermophyton floccosur, Trichophyton mentagrophytes, Trichophyton rubrum, Trichophyton tonsurans, Trichophyton equinum, Dermatophilus congolensis, Microsporum canis, Microsporu audouinii, Microsporum gypseum, Malassezia ovale, Pseudallescheria, Scopulariopsis, Scedosporium*, and *Candida albicans*. Further examples of fungal infectious agent include, but are not limited to, *Aspergillus, Blastomyces dermatitidis, Candida, Coccidioides immitis, Cryptococcus neoformans, Histoplasma capsulatum* var. *capsulatum, Paracoccidioides brasiliensis, Sporothrix schenckii, Zygomycetes* spp., *Absidia corymbifera, Rhizomucor pusillus*, or *Rhizopus arrhizus*.

The biological sample may comprise one or more parasites. Non-limiting examples of parasites include *Plasmodium, Leishmania, Babesia, Treponema, Borrelia, Trypanosoma, Toxoplasma gondii, Plasmodium falciparum, P. vivax, P. ovale, P. malariae, Trypanosoma* spp., or *Legionella* spp. In some cases, the parasite is *Trichomonas vaginalis*.

In some cases, the biological sample is a sample taken from a subject infected with or suspected of being infected with an infectious agent (e.g., bacteria, virus). In some aspects, the biological sample comprises an infectious agent associated with a sexually-transmitted disease (STD) or a sexually-transmitted infection (STI). Non-limiting examples of STDs or STIs and associated infectious agents that may be detected with the devices and methods provided herein may include, Bacterial Vaginosis; Chlamydia (*Chlamydia trachomatis*); Genital herpes (herpes virus); Gonorrhea (*Neisseria gonorrhoeae*); Hepatitis B (Hepatitis B virus); Hepatitis C (Hepatitis C virus); Genital Warts, Anal Warts, Cervical Cancer (Human Papillomavirus); Lymphogranuloma venereum (*Chlamydia trachomatis*); Syphilis (*Treponema pallidum*); Trichomoniasis (*Trichomonas vaginalis*); Yeast infection (*Candida*); and Acquired Immunodeficiency Syndrome (Human Immunodeficiency Virus).

In some cases, the sample can be from an environmental source or an industrial source. Examples of environmental sources include, but are not limited to, agricultural fields, lakes, rivers, water reservoirs, air vents, walls, roofs, soil samples, plants, and swimming pools. Examples of industrial sources include, but are not limited to clean rooms, hospitals, food processing areas, food production areas, food stuffs, medical laboratories, pharmacies, and pharmaceutical compounding centers. The sample can be a forensic sample (e.g., hair, blood, semen, saliva, etc.). The sample can comprise an agent used in a bioterrorist attack (e.g., influenza, anthrax, smallpox).

In some cases, more than one sample can be obtained from a subject or source, and multiple immunoassay tests using a single sensing device or apparatus described herein can be performed. In some cases, 2, 3, 4, 5, 6, 7, 8, 9, 10, 15, 20, 25, 30, 35, 40, 45, 50 or more samples can be obtained. In some cases, more than one sample may be obtained over a period of time, for example, to monitor disease progression or to monitor a biological state or condition (e.g., cardiac conditions). Generally, the sensing devices of the disclosure are configured for repeated or continuous use. Alternatively, the sensing devices can be one-time use (e.g., disposable).

In some cases, the subject is affected by a genetic disease, a carrier for a genetic disease or at risk for developing or passing down a genetic disease, where a genetic disease is any disease that can be linked to a genetic variation such as mutations, insertions, additions, deletions, translocation, point mutation, trinucleotide repeat disorders and/or single nucleotide polymorphisms (SNPs).

The biological sample can be from a subject who has a specific disease, disorder, or condition, or is suspected of having (or at risk of having) a specific disease, disorder or condition. For example, the biological sample can be from a cancer patient, a patient suspected of having cancer, or a patient at risk of having cancer. The cancer can be, e.g., acute lymphoblastic leukemia (ALL), acute myeloid leukemia (AML), adrenocortical carcinoma, Kaposi Sarcoma, anal cancer, basal cell carcinoma, bile duct cancer, bladder cancer, bone cancer, osteosarcoma, malignant fibrous histiocytoma, brain stem glioma, brain cancer, craniopharyngioma, ependymoblastoma, ependymoma, medulloblastoma, medulloepithelioma, pineal parenchymal tumor, breast cancer, bronchial tumor, Burkitt lymphoma, Non-Hodgkin lymphoma, carcinoid tumor, cervical cancer, chordoma, chronic lymphocytic leukemia (CLL), chronic myelogenous leukemia (CML), colon cancer, colorectal cancer, cutaneous T-cell lymphoma, ductal carcinoma in situ, endometrial cancer, esophageal cancer, Ewing Sarcoma, eye cancer, intraocular melanoma, retinoblastoma, fibrous histiocytoma, gallbladder cancer, gastric cancer, glioma, hairy cell leukemia, head and neck cancer, heart cancer, hepatocellular (liver) cancer, Hodgkin lymphoma, hypopharyngeal cancer, kidney cancer, laryngeal cancer, lip cancer, oral cavity cancer, lung cancer, non-small cell carcinoma, small cell carcinoma, melanoma, mouth cancer, myelodysplastic syndromes, multiple myeloma, medulloblastoma, nasal cavity cancer, paranasal sinus cancer, neuroblastoma, nasopharyngeal cancer, oral cancer, oropharyngeal cancer, osteosarcoma, ovarian cancer, pancreatic cancer, papillomatosis, paraganglioma, parathyroid cancer, penile cancer, pharyngeal cancer, pituitary tumor, plasma cell neoplasm, prostate cancer, rectal cancer, renal cell cancer, rhabdomyosarcoma, salivary gland cancer, Sezary syndrome, skin cancer, nonmelanoma, small intestine cancer, soft tissue sarcoma, squamous cell carcinoma, testicular cancer, throat cancer, thymoma, thyroid cancer, urethral cancer, uterine cancer, uterine sarcoma, vaginal cancer, vulvar cancer, Waldenstrom Macroglobulinemia, or Wilms Tumor. The sample can be from the cancer and/or normal tissue from the cancer patient. In some cases, the sample is a biopsy of a tumor.

The biological sample can be processed to render it competent for performing any of the methods using any of the devices or kits provided herein. For example, a solid sample may be dissolved in a liquid medium or otherwise prepared as a liquid sample to facilitate flow along the test strip of the device. In such cases where biological cells or particles are used, the biological cells or particles may be lysed or otherwise disrupted such that the contents of the cells or particles are released into a liquid medium. Molecules contained in cell membranes and/or cell walls may also be released into the liquid medium in such cases. A liquid medium may include water, saline, cell-culture medium, or any solution and may contain any number of salts, surfactants, buffers, reducing agents, denaturants, preservatives, and the like.

Generally, the sample contains or is suspected of containing one or more target analytes. In various aspects, the sample may contain at least a first analyte and a second analyte. The term "analyte" as used herein may refer to any substance that is to be analyzed using the methods and devices provided herein. The immunoassay sensing devices and arrays disclosed herein may be configured to simultaneously detect the presence of 1, 2, 3, 4, 5, 6, 7, 8, 9, 10 or more analytes in a sample. The immunoassay sensing devices and arrays disclosed herein can be capable of simultaneous and multiplexed detection of multiple target analytes in a single sample.

Non-limiting examples of analytes may include proteins, cytokines, chemokines, haptens, immunoglobulins, hormones, polynucleotides, steroids, drugs, infectious disease agents (e.g., of bacterial or viral origin), drugs of abuse, environmental agents, biological markers, and the like. In one case, the immunoassay detects at least a first analyte, wherein the first analyte is luteinizing hormone (LH). In another case, the immunoassay detects at least a first analyte, wherein the first analyte is human chorionic gonadotropin (hCG). In another case, the immunoassay detects at least a first analyte and a second analyte, wherein the first analyte is estrone-3-glucoronide (E3G) and the second analyte is luteinizing hormone (LH). In another case, the immunoassay detects at least a first analyte and a second analyte, wherein the first analyte is a surface antigen on a first viral particle (e.g., Influenza A) and the second analyte is a surface antigen on a second viral particle (e.g., Influenza B). In another case, the immunoassay detects at least a first analyte, wherein the first analyte is 25-hydroxyvitamin D, 25-hydroxyvitamin D2 [25(OH)D$_2$], or 25-hydroxyvitamin D3 [25(OH)D$_3$]. In another case, the immunoassay detects at least a first analyte and a second analyte, wherein the first analyte is triiodothyronine (T3) and the second analyte is thyroxine (T4). In another case, the immunoassay detects at least a first analyte, wherein the first analyte is an allergen. Non-limiting examples of allergens may include: Balsam of Peru, fruit, rice, garlic, oats, meat, milk, peanuts, fish, shellfish, soy, tree nuts, wheat, hot peppers, gluten, eggs, tartrazine, sulfites, tetracycline, phenytoin, carbamazepine, penicillin, cephalosporins, sulfonamides, non-steroidal anti-inflammatories (e.g., cromolyn sodium, nedocromil sodium, etc.), intravenous contrast dye, local anesthetics, pollen, cat allergens, dog allergens, insect stings, mold, perfume, cosmetics, semen, latex, water, house dust mites, nickel, gold, chromium, cobalt chloride, formaldehyde, photographic developers, fungicide, dimethylaminopropylamine, para-phenylenediamine, glyceryl monothioglycolate, toluene-sulfonomide formaldehyde.

The sensing device may be used to test for the presence or absence of at least a first analyte and a second analyte in a sample. In some cases, the sensing device may be used to determine an amount or a relative amount of at least a first and second analyte in a sample.

The presence or absence of analytes may be indicative of a disease or disorder in a subject. The presence or absence of analytes may be indicative of a biological state or condition of a subject. In some cases, the presence or absence of analytes indicates that a subject has or is at risk of developing a disease. In some cases, the presence or absence of analytes indicates that a subject has a disorder (e.g., thyroid disorder). In some cases, the presence or absence of analytes indicates that a subject has a deficiency (e.g., vitamin deficiency). In some cases, the presence or absence of analytes indicates that a product (e.g., a food or drink product) contains an allergen.

The sensing device 1100 may be an electrochemical sensing device configured for both catalytic and affinity-based detection of one or more target analytes in a sample. A catalytic sensor(s) or catalytic sensing utilizes molecules (such as enzymes) that catalyze a biochemical reaction on the sensing surface with the target molecule and detection based on the resulting products. An affinity-based sensor(s) or affinity-based sensing is designed to monitor binding of the target molecule and uses other specific binding molecules (e.g., proteins, lectins, receptors, nucleic acids, whole cells, aptamers, DNA/RNA, antibodies or antibody-related substances, etc.) for biomolecular recognition.

In many embodiments, the sensing devices or arrays disclosed herein can be configured to simultaneously detect and quantitate different isoforms of a single protein. The molecules associated with the catalysis-based reaction may be anchored onto the sensing surface (e.g. working electrode) through an affinity-based mechanism to ensure that the chemical reaction(s) occurs in proximity of the sensing surface for enhanced sensitivity of detection. The output electrical signals for both catalytic and affinity sensors/sensing is measured in current, voltage, and impedance.

Amperometric (i.e. DC current—DC voltage—time) and impedimetric sensors are electroanalytical methods for characterization of the surface phenomena and changes at the sensing electrode surfaces. Amperometric sensors can measure changes to electric current resulting from either catalytic mechanisms and/or affinity binding mechanisms occurring at the sensing electrode surfaces under an applied field/potential and that are related to the concentration of the target species or analytes present in the solution. Voltammetry and chronoamperometry are subclasses of amperometry. In voltammetry, current is measured by varying the potential applied to the sensing electrode. In chronoamperometry, current is measured at a fixed potential, at different times after the start of sensing.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Figure 12A:
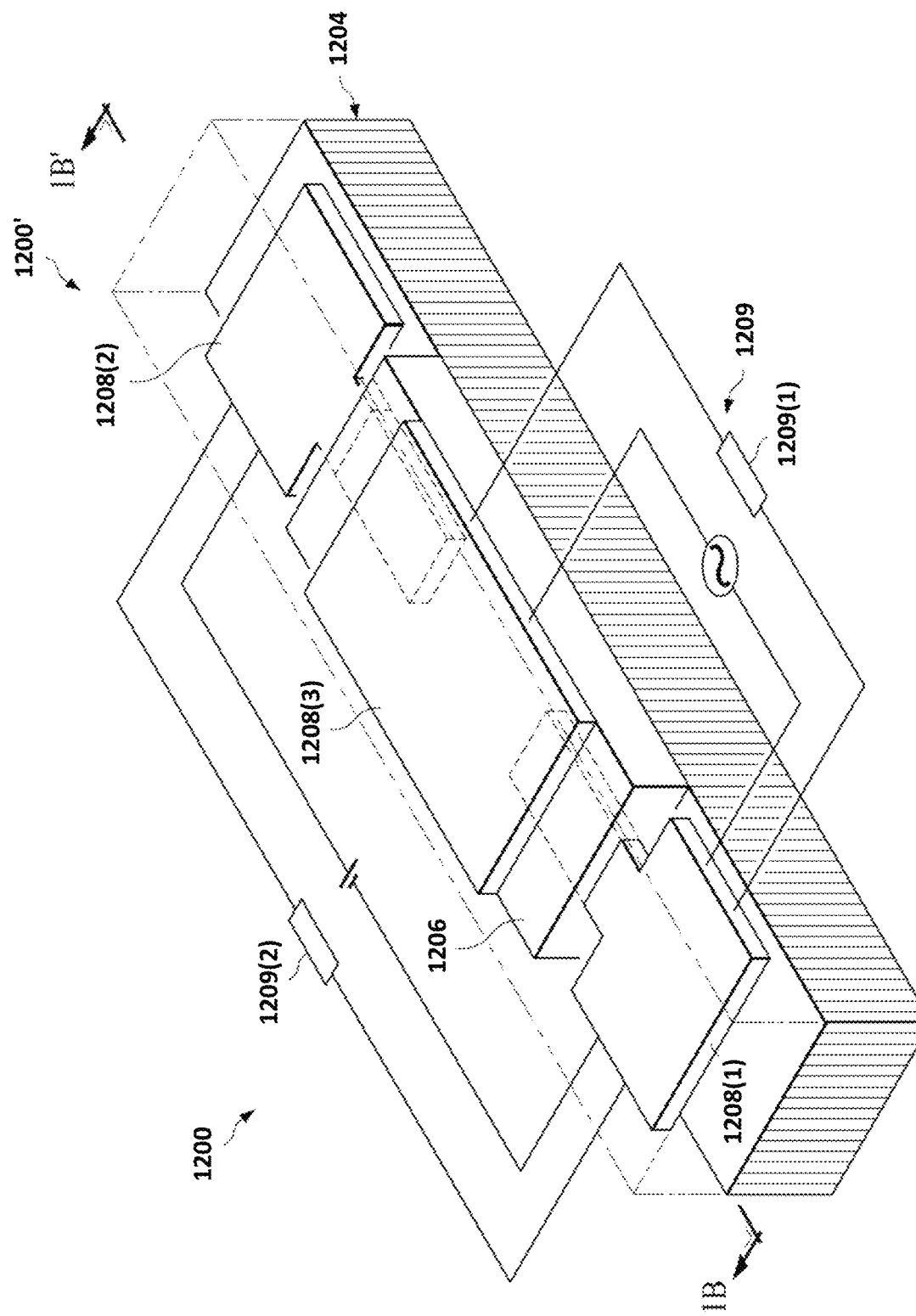
FIGS. 12A-C are schematic diagrams of another example sensing device in accordance with embodiments of the present disclosure.
Figure 12B:
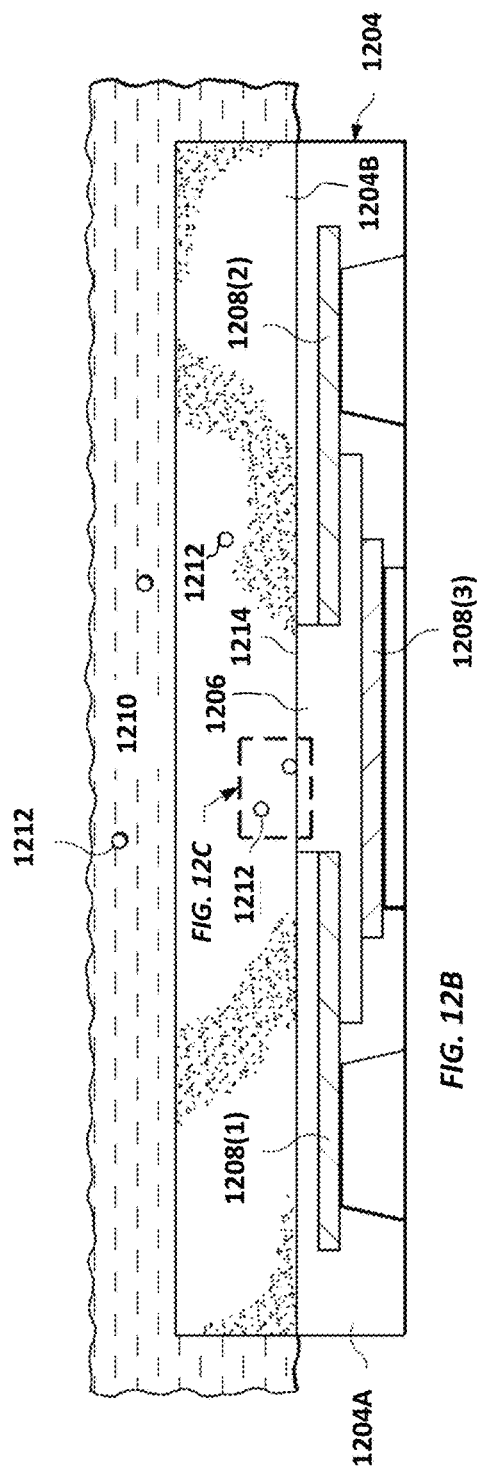
Figure 12C:
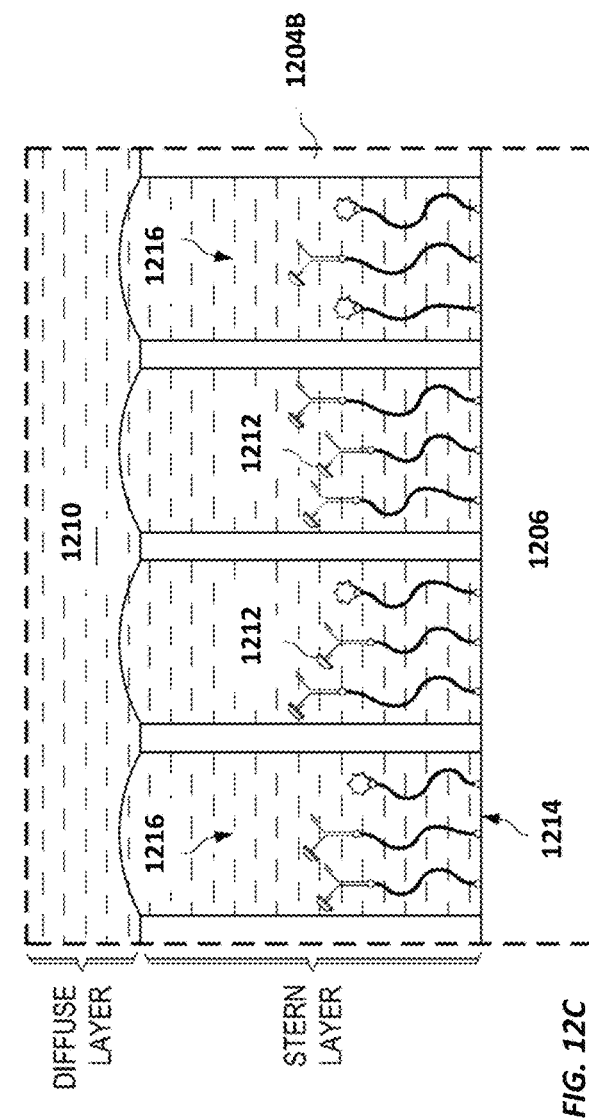

FIG. 12A is a schematic diagram illustrating a biosensing system 1200 for facilitating biosensing using electron-ionic mechanisms at fluid-sensor interfaces in accordance with one example embodiment. FIG. 12B is a schematic diagram of a cross-section along axis B-B' in accordance with embodiments of the present disclosure. FIG. 12C is a schematic diagram of an example detail of the cross-section in accordance with embodiments of the present disclosure.

FIG. 12A illustrates a biosensing system 1200 that includes a biosensor 1202 including a substrate 1204, a sensing element 1206, a plurality of electrodes 1208(1)-1208(3), and an output 1209 comprised of two components, baseline 1209(1) and response 1209(2).

A transverse voltage may be applied across some of electrodes 1208 (e.g., 1208(1) and 1208(2)); an orthogonal voltage may be applied across other electrodes 1208 (e.g., 1208(1) and 1208(3)). Electrodes 1208 (e.g., 1208(1) and 1208(2)) across which the transverse voltage is applied may be referred to as 'transverse electrode;' electrodes 1208 (e.g., 1208(1) and 1208(3)) across which the orthogonal voltage is applied may be referred to as 'orthogonal electrodes.' In a general sense, 'transverse' and 'orthogonal' refer to direction of electric fields produced by the respective voltages; in various embodiments, the electric field produced by the transverse voltage is perpendicular to the electric field produced by the orthogonal voltage. In some embodiments, the transverse voltage may comprise direct current (DC) voltage and the orthogonal voltage may comprise alternating current (AC) voltage. In other embodiments, the transverse voltage may comprise AC voltage, and the orthogonal voltage may comprise DC voltage. In yet other embodiments, the transverse voltage may initially comprise AC voltage, which may be switched to DC voltage, and the orthogonal voltage may comprise AC voltage.

Baseline 1209(1) comprises impedance, or capacitance, or current measured across orthogonal electrodes 1208(1) and 1208(3) and establishes a baseline value for the respective measurement; response 1209(2) comprises impedance, or capacitance, or current measured across transverse electrodes 1208(1) and 1208(2). In various embodiments, comparison between baseline 1209(1) and response 1209(2) can indicate a signal-to-noise ratio (SNR) of the measurements and provide detection and/or measurement of concentration of an analyte 1212 in a fluid 1210.

Substrate 1204 generally allows for fluid containment such that a portion of fluid 1210 comprising analyte 1212 is in contact with sensing element 1206 at a fluid-sensor interface 1214. Note that fluid containment is in three dimensions, for example, both vertically and laterally (e.g., perpendicular and parallel to sensing element surface). Fluid-sensor interface 1214 comprises a zone of interaction between sensing element 1206 and fluid 1210. In some embodiments, fluid-sensor interface 1214 comprises a surface of sensing element 1206 in contact with fluid 1210; in other embodiments, fluid-sensor interface 1214 comprises an additional layer of linker molecules that are bound to the surface of sensing element 1206; in yet other embodiments, fluid-sensor interface 1214 comprises an additional layer of capture probes that bind to the linker molecules. In yet other embodiments, fluid-sensor interface 1214 additionally comprises a layer of fluid 1210 including an electrical double layer (EDL).

In some embodiments, as indicated in FIG. 12B, substrate 1204 may comprise two separate portions, indicated as 1204A and 1204B. In an example embodiment, portion 1204A comprises a hydrophobic biocompatible material (e.g., Parylene™) and portion 1204B comprises a porous biocompatible hydrophilic membrane (e.g., polyimide, polyamide, nylon, alumina, polycarbonate, polymer, ceramic, etc.). In various embodiments, portion 1204A may prevent direct interaction between fluid 1210 and electrodes 1208(1)-1208(3), for example, providing dielectric separation (e.g., electrical isolation) of electrodes 1208(1)-1208(3) from fluid 1210. In some embodiments, portion 1204B may provide a fluid containment zone allowing analyte 1212 of fluid 1210 to bind to sensing element 1206 at fluid-sensor interface 1214.

Some of electrodes 1208(1)-1208(3) (e.g., 1208(1) and 1208(2)) may be located on one plane, and the other electrodes (e.g., 1208(3)) may be located on another, different plane. In an example embodiment, transverse electrodes 1208(1) and 1208(2) may be located on a first plane of sensing element 1206 and orthogonal electrode 1208(3) may be located on a second plane of sensing element 1206 parallel to and removed from the first plane.

To explain the fluid containment in more detail, as indicated in FIG. 12C, portion 1204B may include pores 1216 that provide a fluid containment zone allowing analyte 1212 to bind to sensing element 1206 at fluid-sensor interface 1214 in the presence of an electric field. In some embodiments, pores 1216 may comprise nanopores (e.g., diameter or size in the order of nanometers). In various embodiments, the electric field produced by the orthogonal voltage causes reversible aggregation of analyte 1212 in fluid 1210 into planar aggregates adjacent to fluid-sensor interface 1214. The planar aggregation disassembles when the electric field is removed. In confined geometries, as in pores 1216, the surface charge distribution on sensing element 1206 and topography of bounding electrodes 1208(1) and 1208(2) may determine a nature of electron-ion interaction at fluid-sensor interface 1214. The planar aggregation can include organization similar to self-assembly producing partial coverage, monolayer coverage or stretched coverage.

In various embodiments, fluid 1210 wicks through pores 1216 to make contact with sensing element 1206 at fluid-sensor interface 1214. In a general sense, when sensing element 1206 having surface charge is immersed in fluid 1210 containing ions, a diffuse ion cloud, called the "stern layer" forms in fluid 1210 to screen (e.g., neutralize) sensing element 1206's surface charge. Beyond the stern layer is a diffuse layer comprising ions providing an electrical gradient within fluid 1210. The arrangement of a layer of (immobile) charges in the stern layer and the screening cloud of (mobile) counter-ions in the diffuse layer of fluid 1210 is referred to as the electrical double layer (EDL). As noted previously, fluid-sensor interface 1214 comprises the EDL. In the EDL of small but finite thickness, fluid 1210 is not electroneutral. Consequently, electric fields acting on the EDL will set in motion ions in the diffuse layer, and these will in turn entrain surrounding fluid 1210. The resulting flow fields reflect the spatial distribution of ionic current in fluid 1210.

The diffuse layer may be polarized by the orthogonal electric field (i.e., the electric field produced by the orthogonal voltage) to effect charge perturbation associated with detection of target species of analyte 1212 in fluid 1210. The effective ionic content of the combination of the stern layer and the diffuse layer acts as a screen (e.g., charge screening) preventing the target species of analyte 1212 from travelling to and binding to sensing element 1206. However, excluded volume effect (e.g., 'excluded volume' of a molecule is the volume that is inaccessible to other molecules in the system as a result of the presence of the molecule) and macromolecular crowding from non-specific target species in the confined spaces (e.g., pores 1216) can minimize such charge screening. Embodiments of biosensing system 1200 can facilitate multiple target species detection in varying fluids; analyte 1212 may comprise target species with no charge, high charge or low charge and fluid 1210 may have with varying polarity levels within the broad scope of the embodiments.

Figure 13:
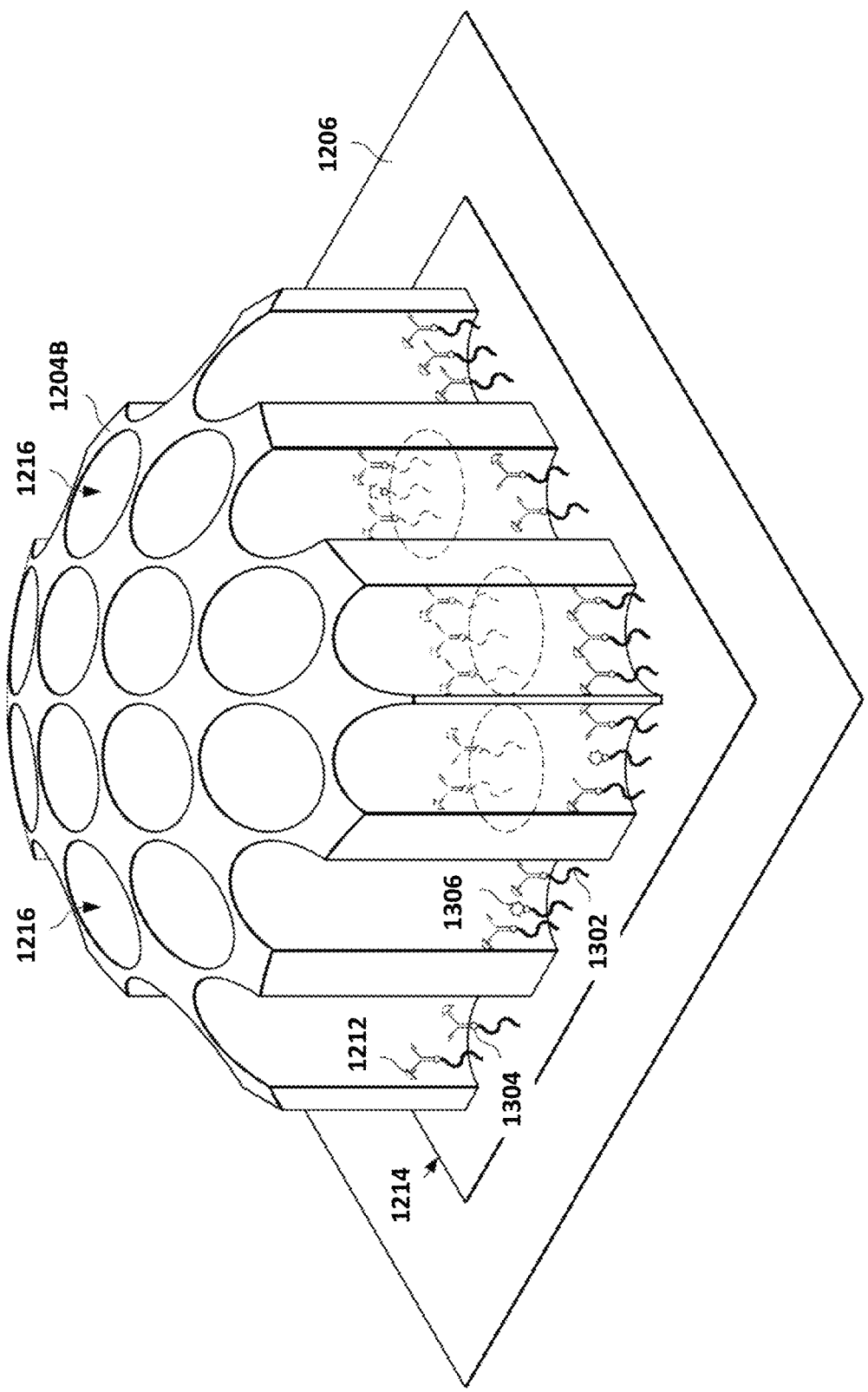
FIG. 13 is a schematic block diagram illustrating example details associated with binding according to an embodiment of biosensing system shown in FIGS. 12A-C.

Turning to FIG. 13, FIG. 13 is a simplified block diagram illustrating example details associated with binding according to an embodiment of biosensing system 1200. Based on the method and physical conditions used for deposition of sensing element 1206, selective surface tuning can be achieved thereon, for example, to enhance sensitivity of biosensor 1202 to specific target species of analyte 1212. In an example embodiment, in which sensing element 1206 comprises ZnO, enriched zinc terminated sites or enriched oxygen terminated sites may be deposited on ZnO, for example. The Zn-terminated site and the O-terminated sites can influence immobilizing of biomolecular capture probes based on preferential binding of linker molecules to either Zn-terminated sites or O-terminated sites. Such mechanisms can improve efficiency and sensitivity of biosensor 1202. Note that other embodiments can include Graphene oxide or $MoS_2$ instead of ZnO.

In some embodiments, analyte 1212 may bind directly to sensing element 1206 at fluid-sensor interface 1214. In other embodiments, to achieve affinity binding of target species, the surface of sensing element 16 comprising fluid-sensor interface 1214 is functionalized with various linker molecules 1302. Analyte 1212 binds to linker molecules 1302, effecting charge modulation at fluid-sensor interface 1214. Dithiobis succinidyl propionate is an example of a thiol linker molecule 1302. Any other suitable linker molecule, such as carboxylic molecules, hydroxyl molecules, etc. may be used within the broad scope of the embodiments.

In yet other embodiments, to achieve affinity binding of target species, the surface of sensing element 1206 comprising fluid-sensor interface 1214 is functionalized with various linker molecules 1302, to which capture probes 1304 are bound. Although additional molecules may be bound to capture probes 1304, and so on, beyond three levels of binding, the charge modulation and characterization signal may become weak and difficult to isolate from noise, affecting sensitivity of biosensor 1202. Capture probes 1304 may connect linker molecules 1302, which are attached to the surface of sensing element 1206, to analyte 1212. Examples of capture probes 704 includes aptamers, antibodies, enzymes, peptides, and amino acid and nucleic acid sequences.

In some embodiments, blocking molecules 1306 may neutralize linker molecules 1302 without capture probes 1304 and minimize binding of interfering species that can cause signal attenuation and cross-reactivity responses. Examples of blocking molecules 1306 include Super-Block™, albumin-based solutions that can block unbound organic—NH groups on linker molecules 1302.

Note that for ease of illustration, pore 1216 is illustrated as a through-hole pore. Various other pore configurations may be included within the broad scope of the embodiments. For example, pore 1216 may comprise intercalated pores in some embodiments. In other embodiments, pore 1216 may comprise hierarchical pores (e.g., pore in pore). Various commercially available materials may be used to fabricate substrate 1204 to include suitable pore configurations. For example, Merocel™. is one of a commercially available porous material of the intercalated "sponge" like material. Other commercially available materials include those sold by Whatman Membranes™. from GE Life Sciences™, Advantec™, etc. Hierarchical pores may be seen in diatoms, and similar pore configuration used in synthesizing appropriate substrate materials.

Turning to FIG. 14, FIG. 14 is a simplified diagram illustrating example operations 1400 and details according to an embodiment of biosensing system 1200. At 1402, linker molecule 1302 (e.g., dithiobis succinimidyl propionate) may be bound to the surface of sensing element 1206 at fluid-sensor interface 1214, comprising the surface of sensing element 16 that can be exposed to fluid 1210. At 1404, a saturating concentration (e.g., maximum concentration loadable onto sensing element 1206) of capture probes 1304 may be inoculated (e.g., introduced, such as with a fixed volume of solution, in a metered manner) on biosensor 1202. Capture probes 1304 bind to at least some linker molecules 1302. At 1406, non-specific binding noise may be avoided by adding a blocking buffer containing blocking molecules 1308. At 1408, varying concentrations of analyte 1212 (e.g., protein biomarkers) are inoculated and impedance response is studied to generate a calibration chart.

An example cross-section is also shown, comprising gold electrode 1208(3) in Ohmic contact with n-type metal oxide semiconductor sensing element 1206, which is in contact with fluid 1210. The electrical voltage supplied to sensing element 1206 may provide sufficient energy to polarize fluid 1210 and activate sensing element 1206. Charge depletion layer 1412 and electrical double layer (EDL) 1410 may vary in size and electrical properties based on the binding interaction between analyte 1212 and sensing element 1206 at fluid-sensor interface 1214. Note that charge depletion layer 1412 indicates modulation of electro-ionic charge distribution at fluid-sensor interface 1214. In the example embodiment shown, sensing element 1206 is a n-type semiconductor and at steady state, the energy bands of the semiconductor material of sensing element 1206 are bent to align Fermi levels, resulting in charge build-up on the semiconductor side of fluid-sensor interface 1214. Charge depletion layer 1412 may also be referred to in this Specification as the "space charge" region. Conversely, for a p-type semiconductor material of sensing element 1206, the space charge region is formed by energy band bending in the opposite direction. In a general sense, the space charge region forms in response to distortion of the semiconductor material's valence and conduction bands ("band bending") in the vicinity of fluid-sensor interface 1214.

Figure 15:
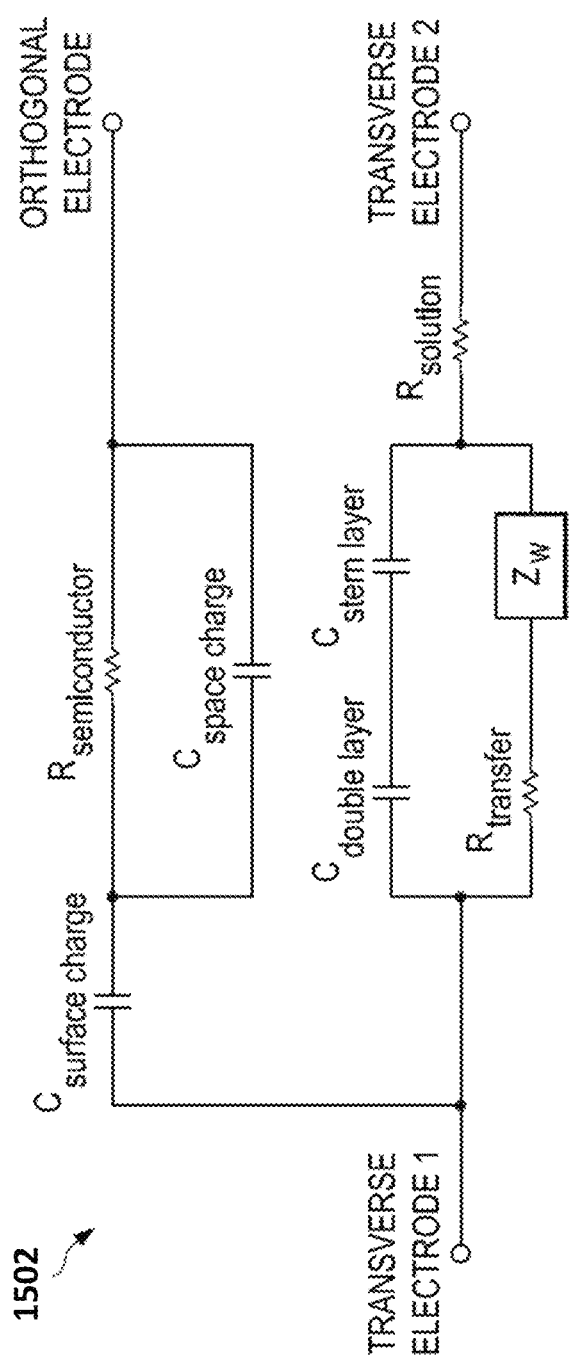
FIG. 15 is a schematic diagram illustrating an example circuit model according to an embodiment of a biosensing system as shown in FIGS. 12A-C.

Turning to FIG. 15, FIG. 15 is a simplified diagram illustrating an example circuit model 1502 according to an embodiment of biosensing system 1200. Equivalent circuit model 1502 can be used to represent the three-electrode configuration of biosensor 1202 and comprehend output 1209 comprising an analog signal measured at electrodes 1208(1)-1208(3). $C_{surface\ charge}$ represents capacitance of the surface charges at fluid-sensor interface 1214; $R_{semiconductor}$ represents resistance of sensing element 1206; and $C_{space\ charge}$ represents capacitance of a charge depletion layer 1412. $C_{surface\ charge}$, $R_{semiconductor}$ and $C_{space\ charge}$ influence signal output from biosensor 12 at orthogonal electrode 18(3). $C_{double\ layer}$, represents the capacitance of EDL 1410; $C_{stern\ layer}$ represents capacitance of the Stern layer in a fluid 1210; $R_{transfer}$ and $Z_w$ represent resistive parameters of a fluid 1210 fluid-sensor interface 1214 that influence signal output from biosensor 1202 as measured at transverse electrodes 1208(1) and 1208(2).

Note that in this Specification, references to various features (e.g., elements, structures, modules, components, steps, operations, characteristics, etc.) included in "one embodiment", "example embodiment", "an embodiment", "another embodiment", "some embodiments", "various embodiments", "other embodiments", "alternative embodiment", and the like are intended to mean that any such features are included in one or more embodiments of the present disclosure, but may or may not necessarily be combined in the same embodiments. Furthermore, the words "optimize," "optimization," and related terms are terms of art that refer to improvements in speed and/or efficiency of a specified outcome and do not purport to indicate that a process for achieving the specified outcome has achieved, or is capable of achieving, an "optimal" or perfectly speedy/perfectly efficient state.

In example implementations, at least some portions of analyzing activities outlined herein may be implemented in software, for example, within sensor engine 120. In some embodiments, one or more of these features may be implemented in hardware, provided external to these elements, or consolidated in any appropriate manner to achieve the intended functionality. The various circuit elements may include software (or reciprocating software) that can coordinate in order to achieve the operations as outlined herein. In still other embodiments, these elements may include any suitable algorithms, hardware, software, components, modules, interfaces, or objects that facilitate the operations thereof.

In a general sense, the arrangements depicted in the FIGURES may be more logical in their representations, whereas a physical architecture may include various permutations, combinations, and/or hybrids of these elements. It is imperative to note that countless possible design configurations can be used to achieve the operational objectives outlined here. Accordingly, the associated infrastructure has a myriad of substitute arrangements, design choices, device possibilities, hardware configurations, software implementations, equipment options, etc.

In some of example embodiments, one or more memory elements can store data used for the operations described herein. This includes the memory element being able to store instructions (e.g., software, logic, code, etc.) in non-transitory media, such that the instructions are executed to carry out the activities described in this Specification. A processor can execute any type of instructions associated with the data to achieve the operations detailed herein in this Specification. In one example, processors could transform an element or an article (e.g., data) from one state or thing to another state or thing. In another example, the activities outlined herein may be implemented with fixed logic or programmable logic (e.g., software/computer instructions executed by a processor) and the elements identified herein could be some type of a programmable processor, programmable digital logic (e.g., a field programmable gate array (FPGA), an erasable programmable read only memory (EPROM), an electrically erasable programmable read only memory (EEPROM)), an ASIC that includes digital logic, software, code, electronic instructions, flash memory, optical disks, CD-ROMs, DVD ROMs, magnetic or optical cards, other types of machine-readable mediums suitable for storing electronic instructions, or any suitable combination thereof.

These devices may further keep information in any suitable type of non-transitory storage medium (e.g., random access memory (RAM), read only memory (ROM), field programmable gate array (FPGA), erasable programmable read only memory (EPROM), electrically erasable programmable ROM (EEPROM), etc.), software, hardware, or in any other suitable component, device, element, or object where appropriate and based on particular needs. The information being tracked, sent, received, or stored in biosensing system 1200 could be provided in any database, register, table, cache, queue, control list, or storage structure, based on particular needs and implementations, all of which could be referenced in any suitable timeframe. Any of the memory items discussed herein should be construed as being encompassed within the broad term 'memory element.' Similarly, any of the potential processing elements, modules, and machines described in this Specification should be construed as being encompassed within the broad term 'processor.'

It is also important to note that the operations and steps described with reference to the preceding FIGURES illustrate only some of the possible scenarios that may be executed by, or within, the system. Some of these operations may be deleted or removed where appropriate, or these steps may be modified or changed considerably without departing from the scope of the discussed concepts. In addition, the timing of these operations may be altered considerably and still achieve the results taught in this disclosure. The preceding operational flows have been offered for purposes of example and discussion. Substantial flexibility is provided by the system in that any suitable arrangements, chronologies, configurations, and timing mechanisms may be provided without departing from the teachings of the discussed concepts.

Although the present disclosure has been described in detail with reference to particular arrangements and configurations, these example configurations and arrangements may be changed significantly without departing from the scope of the present disclosure. For example, although the present disclosure has been described with reference to particular communication exchanges involving certain network access and protocols, biosensing system 1200 may be applicable to other exchanges or routing protocols. Moreover, although biosensing system 1200 has been illustrated with reference to particular elements and operations that facilitate the communication process, these elements, and operations may be replaced by any suitable architecture or process that achieves the intended functionality of biosensing system 1200.

What is claimed is:
1. A wearable device comprising:
an analog multiplexer, the analog multiplexer comprising:
a plurality of impedance circuit elements, each of the plurality of impedance circuit elements comprising a source pin and a sink pin, wherein the sink pin of at least a first one of the plurality of impedance circuit elements is coupled to the source pin of a second one of the plurality of impedance circuit elements; and
a circuit element to generate N selection signals for selecting a signal to be output from the analog multiplexer; and
an analog front end (AFE) to resolve input and output conditions for selecting an output from the analog multiplexer, wherein:
each impedance circuit element in the plurality of impedance circuit elements comprises a sensor configured to detect at least one analyte,
each sensor includes:
at least a first electrode conductively coupled to a first contact pad and a second electrode conductively coupled to a second contact pad, the first contact pad coupled to the source pin of the impedance circuit element and the second contact pad coupled to the sink pin of the impedance circuit element;

semiconducting nanostructures on at least one in the plurality of electrodes; and
a type of capture reagent attached to the semiconducting nanostructures, the type of capture reagent to bind to the at least one analyte, and
different sensors have correspondingly different types of capture reagents to bind to different analytes.

2. The wearable device of claim 1, further comprising a dense matrix equation solver to process signals received from the analog multiplexer.

3. The wearable device of claim 2, wherein the dense matrix equation solver comprises digital logic, and the wearable device further comprises an analog to digital converter between analog multiplexer and the dense matrix equation solver.

4. The wearable device of claim 1, wherein the wearable device houses the analog multiplexer and the AFE.

5. The wearable device of claim 1, wherein the wearable device comprises logic for N analog tri-state pins and $(N/(N-1))/2$ equation solver acceleration.

6. The wearable device of claim 1, wherein the wearable device is coupled to a computing platform across a wireless communications connection.

7. The wearable device of claim 6, wherein the computing platform comprises one of a mobile device, a desktop computer, a remote server, or a laptop computer.

8. The wearable device of claim 1, wherein the impedance circuit elements comprise one or more of a resistance (R), an inductance (L), and/or a capacitance (C).

9. The wearable device of claim 1, wherein the plurality of analytes is in a single biological sample.

10. The wearable device of claim 9, wherein the plurality of sensors comprising a first set of one or more sensors to detect a first analyte and a second set of one or more sensors to detect a second analyte, the first analyte different from the second analyte.

11. The wearable device of claim 9, wherein the plurality of sensors comprises N sensors; and wherein the plurality of analytes comprises N different analytes.

12. An apparatus, comprising:
a plurality of M sensors, each sensor to detect a particular target analyte in a biological sample;
a plurality of N tri-state input/output (I/O) pins conductively coupled to the plurality of M sensors, wherein M is $N(N-1)/2$; and
an analog frontend coupled to the plurality of N tri-state I/O pins,
wherein:
each sensor includes:
at least a first electrode conductively coupled to a first contact pad and a second electrode conductively coupled to a second contact pad, the first contact pad coupled to one of the plurality of N tri-state I/O pins and the second contact pad coupled to another of the plurality of N tri-state I/O pins;
semiconducting nanostructures on at least one in the plurality of electrodes; and
a type of capture reagent attached to the semiconducting nanostructures,
the type of capture reagent to bind to a particular analyte in the plurality of analytes,
different sensors in the plurality of sensors have correspondingly different types of capture reagents,
the analog frontend includes:
an analog input to control a switch network to switch between outputs of the sensors;
an amplifier circuit coupled to the outputs of the sensors; and
a dense matrix equation solver coupled to the amplifier circuit, and
the dense matrix equation solver and the switch network are to operate concurrently to determine target analyte concentrations from the outputs of the sensors.

13. The apparatus of claim 12, wherein the plurality of sensors is in a wearable device.

14. The apparatus of claim 13, wherein the wearable device is connected to a computing platform by a wireless connection.

15. The apparatus of claim 12, wherein the dense matrix equation solver and the switch network operate concurrently according to a high-density analog multiplexing (HDAM) scheme.

16. The apparatus of claim 15, wherein error from noise is eliminated using a system of linear equations that varies according to the HDAM scheme.

17. The apparatus of claim 12, wherein the sensors are connected to corresponding source pins and sink pins in a plurality of layers according to a routing scheme.

18. The apparatus of claim 12, wherein one of the plurality of N tri-state I/O pins of one sensor is coupled to another of the plurality of N tri-state I/O pins of another sensor in the plurality of M sensors.

19. The apparatus of claim 12, wherein the N tri-state I/O pins of a subset of sensors in the plurality of M sensors are not coupled together.

20. The apparatus of claim 12, wherein the sensors are driven and sensed by at least one of 4-wire and P-wire configurations.

* * * * *